United States Patent
Achard et al.

(10) Patent No.: US 6,355,631 B1
(45) Date of Patent: Mar. 12, 2002

(54) PHARMACEUTICAL COMPOSITIONS CONTAINING AZETIDINE DERIVATIVES, NOVEL AZETIDINE DERIVATIVES AND THEIR PREPARATION

(75) Inventors: Daniel Achard; Hervé Bouchard, both of Thiais; Jean Bouquerel, Drancy; Bruno Filoche, Creteil; Serge Grisoni, Choisy le Roi; Augustin Hittinger, Igny; Michael R. Myers, Saint Nom la Breteche, all of (FR)

(73) Assignee: Aventis Pharma S.A., Anthony (FR)

( * ) Notice: Subject to any disclaimer, the term of this patent is extended or adjusted under 35 U.S.C. 154(b) by 0 days.

(21) Appl. No.: 09/798,452

(22) Filed: Mar. 2, 2001

Related U.S. Application Data

(60) Provisional application No. 60/200,059, filed on Apr. 27, 2000.

(30) Foreign Application Priority Data

Mar. 3, 2000 (FR) .............................. 00 02776

(51) Int. Cl.$^7$ ..................... C07D 205/04; A61K 31/397
(52) U.S. Cl. ..................... 514/210.21; 514/210.01; 514/210.19; 514/210.2; 540/1; 546/275.1; 546/276.4; 546/194; 546/309
(58) Field of Search ............... 546/275, 276.4, 546/194, 309; 540/1; 514/210.01, 210.19, 210.2, 210.21

(56) References Cited

U.S. PATENT DOCUMENTS 5,545,636 A * 8/1996 Heath, Jr. et al. ........... 514/214
5,665,719 A * 9/1997 Bock et al. .................... 544/90

FOREIGN PATENT DOCUMENTS

EP 536035 * 9/1992

OTHER PUBLICATIONS

Suzuki et al, Chemical Abstracts, vol. 83, No. 1, Abstract 9760, p. 811, Jul. 1975.*

* cited by examiner

Primary Examiner—Zinna Northington Davis
(74) Attorney, Agent, or Firm—Irving Newman

(57) ABSTRACT

The present invention relates to pharmaceutical compositions containing, as an active ingredient, at least one compound of formula:

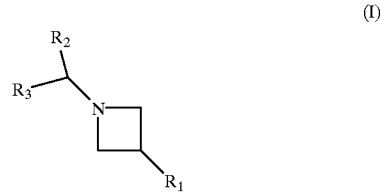

in which $R_1$ represents a radical $—N(R_4)R_5$, $—N(R_4)—CO—R_5$, $—N(R_4)—SO_2R_6$ or one of its pharmaceutically acceptable salts, to the novel derivatives of formula (I), to their pharmaceutically acceptable salts and to their preparation.

21 Claims, No Drawings

PHARMACEUTICAL COMPOSITIONS CONTAINING AZETIDINE DERIVATIVES, NOVEL AZETIDINE DERIVATIVES AND THEIR PREPARATION

This application claims the benefit of U.S. Provisional Application No. 60/200,059, filed Apr. 27, 2000.

The present invention relates to pharmaceutical compositions containing, as active ingredient, at least one compound of formula:

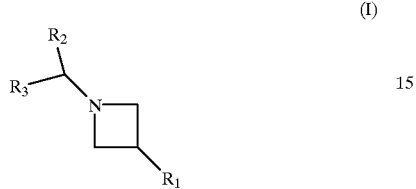

or one of its pharmaceutically acceptable salts, to the novel derivatives of formula (I), to their pharmaceutically acceptable salts and to their preparation.

The compound of formula (I) for which $R_2$ and $R_3$ represent phenyl radicals, $R_1$ represents a radical —N($R_4$)$SO_2R_6$, $R_4$ represents a phenyl radical and $R_6$ represents a methyl radical is described as a synthesis intermediate in patent WO 99/01451. The other compounds and their pharmaceutically acceptable salts are novel and as such form part of the invention.

In formula (I)

$R_1$ represents a radical —N($R_4$)$R_5$, —N($R_4$)—CO—$R_5$, —N($R_4$)—$SO_2R_6$, $R_2$ and $R_3$, which are identical or different, represent either an aromatic chosen from phenyl, naphthyl and indenyl, these aromatics being unsubstituted or substituted with one or more halogen atoms or alkyl, alkoxy, formyl, hydroxyl, trifluoromethyl, trifluoromethoxy, —CO—alk, cyano, —COOH, COOalk, —CONR$_7$R$_8$, —CO—NH—NR$_9$R$_{10}$, alkylsulfanyl, alkylsulfinyl, alkylsulfonyl, alkylsulfanylalkyl, alkylsulfinylalkyl, alkylsulfonylalkyl, hydroxyalkyl or —alk—NR$_7$R$_8$ radicals; or a heteroaromatic chosen from benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidyl, quinolyl, 1,2,3,4-tetrahydroisoquinolyl, thiazolyl and thienyl rings, it being possible for these heteroaromatics to be unsubstituted or substituted with a halogen atom or an alkyl, alkoxy, hydroxyl, trifluoromethyl, trifluoromethoxy, cyano, —COOH, COOalk, —CO—NH—NR$_9$R$_{10}$, —CONR$_7$R$_8$, —alk—NR$_9$R$_{10}$, alkylsulfanyl, alkylsulfinyl, alkylsulfonyl, alkylsulfanylalkyl, alkylsulfinylalkyl, alkylsulfonylalkyl or hydroxyalkyl radical, $R_4$ represents a radical —C($R_{11}$)($R_{12}$)—Het, —Het, —(C$R_{11}$)($R_{12}$)—Ar, Ar, cycloalkyl or norbornyl, $R_5$ represents a hydrogen atom or a hydroxyalkyl, —alk—COOalk, —alk—CONR$_7$R$_8$, —alk—NR$_7$R$_8$, alkoxy, Ar, Het, —CH$_2$Ar, —CH$_2$Het or alkyl radical optionally substituted with one or more halogen atoms, $R_6$ represents a hydroxyalkyl, —alk—COOalk, —alk—CONR$_7$R$_8$, —alk—NR$_7$R$_8$, alkoxy, Ar, Het, —CH$_2$Ar, —CH$_2$Het or alkyl radical optionally substituted with 1 or more halogen atoms, $R_7$ and $R_8$, which are identical or different, represent a hydrogen atom or an alkyl radical or alternatively $R_7$ and $R_8$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, $R_9$ and $R_{10}$, which are identical or different, represent a hydrogen atom or an alkyl, —COOalk, cycloalkyl, alkylcycloalkyl, —alk—O—alk or hydroxyalkyl radical or alternatively $R_9$ and $R_{10}$ together form with the nitrogen atom to which they are attached a 3- to 10-membered saturated or unsaturated mono- or bicyclic heterocycle, optionally containing another heteroatom chosen from oxygen, sulfur and nitrogen and being optionally substituted with one or more alkyl, —COalk, —COOalk, —CO—NHalk, —CS—NHalk, oxo, hydroxyalkyl, —alkyl—O—alk or —CO—NH$_2$ radicals, $R_{11}$ represents a hydrogen atom or a hydroxyalkyl, —alk—COOalk, —alk—CONR$_7$R$_8$, —alk—NR$_7$R$_8$, alkoxyalkyl, Ar, Het, —CH$_2$Ar, —CH$_2$Het or alkyl radical optionally substituted with one or more halogen atoms, $R_{12}$ represents a hydrogen atom or a hydroxyalkyl, —alk—COOalk, —alk—CONR$_7$R$_8$, —alk—NR$_7$R$_8$, alkoxyalkyl or alkyl radical optionally substituted with one or more halogen atoms, or alternatively $R_{11}$ and $R_{12}$ together form with the carbon atom to which they are attached a 3- to 10-membered saturated mono- or bicyclic ring, optionally containing another heteroatom chosen from oxygen, sulfur and nitrogen and being optionally substituted with one or more alkyl radicals, Ar represents a phenyl, naphthyl or indenyl radical, these different radicals being optionally substituted with one or more halogen atoms or alkyl, alkoxy, —CO—alk, cyano, —COOH, —COOalk, —CONR$_{13}$R$_{14}$, —CO—NH—NR$_{15}$R$_{16}$, alkylsulfanyl, alkylsulfinyl, alkylsulfonyl, —alk—NR$_{15}$R$_{16}$, —NR$_{15}$R$_{16}$, alkylthioalkyl, formyl, CF$_3$, OCF$_3$, Het, —O—alk—NH—cycloalkyl, SO$_2$NH$_2$, hydroxyl, hydroxyalkyl, —NHCOalk, NHCOOalk radicals or on 2 adjacent carbon atoms with dioxymethylene, Het represents a 3- to 10-membered unsaturated or saturated mono- or bicyclic heterocycle containing one or more heteroatoms chosen from oxygen, sulfur and nitrogen optionally substituted with one or more halogen atoms or alkyl, alkoxy, alkoxycarbonyl, oxo or hydroxyl radicals, the nitrogen-containing heterocycles being optionally in their N-oxidized form, $R_{13}$ and $R_{14}$, which are identical or different, represent a hydrogen atom or an alkyl radical or alternatively $R_{13}$ and $R_{14}$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, $R_{15}$ and $R_{16}$, which are identical or different, represent a hydrogen atom or an alkyl radical or alternatively $R_{15}$ and $R_{16}$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, alk, represents an alkyl or alkylene radical.

In the preceding definitions and in those which follow, unless otherwise stated, the alkyl and alkylene radicals and portions and the alkoxy radicals and portions are in the form of a straight or branched chain and contain 1 to 6 carbon atoms and the cycloalkyl radicals contain 3 to 10 carbon atoms.

Among the alkyl radicals, there may be mentioned the methyl, ethyl, n-propyl, isopropyl, n-butyl, sec-butyl, isobutyl, tert-butyl, pentyl and hexyl radicals. Among the alkoxy radicals, there may be mentioned the methoxy, ethoxy, n-propoxy, iso-propoxy, n-butoxy, iso-butoxy, sec-butoxy, tert-butoxy and pentyloxy radicals.

Among the cycloalkyl radicals, there may be mentioned in cyclopropyl, cyclobutyl, cyclopentyl and cyclohexyl radicals.

The term halogen comprises chlorine, fluorine, bromine and iodine.

Among the heterocycles represented by Het, the following heterocycles may be mentioned: benzimidazole, benzoxazole, benzothiazole, benzothiophene, cinnoline, thiophene, quinazoline, quinoxaline, quinoline, pyrazole, pyrrole, pyridine, imidazole, indole, isoquinoline, pyrimidine, thiazole, thiadiazole, piperidine, piperazine, triazole, furan, tetrahydroisoquinoline, tetrahydroquinoline, these heterocycles being optionally substituted with one or more halogen atoms or alkyl, alkoxy, alkoxycarbonyl, oxo, hydroxyl, $OCF_3$ or $CF_3$ radicals.

The compounds of formula (I) may be provided in the form of enantiomers and of diastereoisomers. These isomers and mixtures thereof also form part of the invention.

Preferably, the compounds of formula (I) are those for which $R_1$ represents a radical —$N(R_4)R_5$ or —$N(R_4)$—$SO_2R_6$, $R_2$ represents either a phenyl which is unsubstituted or substituted with one or more halogen atoms or alkyl, alkoxy, trifluoromethyl, trifluoromethoxy, —CO—alk, cyano, —$CONR_7R_8$, hydroxyalkyl or —alk—$NR_7R_8$ radicals; or a heteroaromatic chosen from the pyridyl, pyrimidyl, thiazolyl and thienyl rings, it being possible for these heteroaromatics to be unsubstituted or substituted with a halogen atom or an alkyl, alkoxy, hydroxyl, trifluoromethyl, trifluoromethoxy, —$CONR_7R_8$, —alk—$NR_9R_{10}$, alkylsulfanyl, alkylsulfinyl, alkylsulfonyl or hydroxyalkyl radical, $R_3$ represents either a phenyl which is unsubstituted or substituted with one or more halogen atoms or alkyl, alkoxy, trifluoromethyl, trifluoromethoxy, —CO—alk, cyano, —$CONR_7R_8$, hydroxyalkyl or —alk—$NR_7R_8$ radicals; or a heteroaromatic chosen from the pyridyl, pyrimidyl, thiazolyl and thienyl rings, it being possible for these heteroaromatics to be unsubstituted or substituted with a halogen atom or an alkyl, alkoxy, hydroxyl, trifluoromethyl, trifluoromethoxy, —$CONR_7R_8$, —alk—$NR_9R_{10}$, alkylsulfanyl, alkylsulfinyl, alkylsulfonyl or hydroxyalkyl radical, $R_4$ represents a radical —$C(R_{11})(R_{12})$—Het, —Het, —$C(R_{11})(R_{12})$—Ar, Ar or norbornyl, $R_5$ represents a hydrogen atom or a hydroxyalkyl, —alk—COOalk, —alk—$CONR_7R_8$, —alk—$NR_7R_8$, alkoxy, —$CH_2Ar$, —$CH_2Het$ or alkyl radical, $R_6$ represents a hydroxyalkyl, —alk—COOalk, —alk—$CONR_7R_8$, —alk—$NR_7R_8$, alkoxy, —$CH_2Ar$, —$CH_2Het$ or alkyl radical, $R_7$ and $R_8$, which are identical or different, represent a hydrogen atom or an alkyl radical or alternatively $R_7$ and $R_8$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, $R_9$ and $R_{10}$, which are identical or different, represent a hydrogen atom or an alkyl, cycloalkyl, alkylcycloalkyl, —alk—O—alk or hydroxyalkyl radical or alternatively $R_9$ and $R_{10}$ together form with the nitrogen atom to which they are attached a 3- to 10-membered saturated or unsaturated mono- or bicyclic heterocycle, optionally containing another heteroatom chosen from oxygen, sulfur and nitrogen and being optionally substituted with one or more alkyl, —COalkyl, —COOalk, —CO—NHalk, oxo, hydroxyalkyl or —CO—$NH_2$ radicals, $R_{11}$ represents a hydrogen atom or a hydroxyalkyl, —alk—COOalk, —alk—$CONR_7R_8$, —alk—$NR_7R_8$, alkoxyalkyl, Ar, Het, —$CH_2Ar$, —$CH_2Het$ or alkyl radical optionally substituted with one or more halogen atoms, $R_{12}$ represents a hydrogen atom or a hydroxyalkyl, —alk—COOalk, —alk—$CONR_7R_8$, —alk—$NR_7R_8$, alkoxyalkyl or alkyl radical optionally substituted with one or more halogen atoms, or alternatively $R_{11}$ and $R_{12}$ together form with the carbon atom to which they are attached a 3- to 10-membered saturated mono- or bicyclic ring, optionally containing another heteroatom chosen from oxygen, sulfur and nitrogen and being optionally substituted with one or more alkyl radicals, Ar represents a phenyl or naphthyl radical, these different radicals being optionally substituted with one or more halogen atoms or alkyl, alkoxy, —CO—alk, cyano, —$CONR_{13}R_{14}$, alkylsulfonyl, —alk—$NR_{15}R_{16}$, —$NR_{15}R_{16}$, $CF_3$, $OCF_3$, $SO_2NH$, hydroxyl or hydroxyalkyl radicals or on 2 adjacent carbon atoms with dioxymethylene, Het represents a 3- to 10-membered unsaturated or saturated mono- or bicyclic heterocycle containing one or more heteroatoms chosen from oxygen, sulfur and nitrogen optionally substituted with one or more halogen atoms or alkyl, alkoxy, oxo or hydroxyl radicals, the nitrogen-containing heterocycles being optionally in their N-oxidized form and, more particularly, Het represents a heterocycle chosen from benzimidazole, benzoxazole, benzothiazole, benzothiophene, thiophene, quinazoline, quinoxaline, quinoline, pyrrole, pyridine, imidazole, indole, isoquinoline, pyrimidine, thiazole, thiadiazole, furan, tetrahydroisoquinoline and tetrahydroquinoline, these heterocycles being optionally substituted with one or more halogen atoms or alkyl, alkoxy, alkoxycarbonyl, oxo, hydroxyl, $OCF_3$ or $CF_3$ radicals.

$R_{13}$ and $R_{14}$, which are identical or different, represent a hydrogen atom or an alkyl radical or alternatively $R_{13}$ and $R_{14}$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, $R_{15}$ and $R_{16}$, which are identical or different, represent a hydrogen atom or an alkyl radical or alternatively $R_{15}$ and $R_{16}$ together form with the nitrogen atom to which they are attached a 3- to 10-membered saturated monoor bicyclic heterocycle, optionally containing another heteroatom chosen from oxygen, sulfur and nitrogen and being optionally substituted with one or more alkyl radicals.

Still more preferably, the compounds of formula (I) are chosen from the following compounds:

$R_1$ represents a radical —N($R_4$)—SO$_2R_6$, $R_2$ represents either a phenyl which is unsubstituted or substituted with one or more halogen atoms or alkyl, alkoxy, trifluoromethyl, trifluoromethoxy, cyano, —CONR$_7$R$_8$, hydroxyalkyl or —alk—NR$_7$R$_8$ radicals; or a heteroaromatic chosen from the pyridyl, pyrimidyl, thiazolyl and thienyl rings, it being possible for these heteroaromatics to be unsubstituted or substituted with a halogen atom or an alkyl, alkoxy, hydroxyl, trifluoromethyl, trifluoromethoxy, —CONR$_7$R$_8$ or hydroxyalkyl radical, $R_3$ represents either a phenyl which is unsubstituted or substituted with one or more halogen atoms or alkyl, alkoxy, trifluoromethyl, trifluoromethoxy, cyano, —CONR$_7$R$_8$, hydroxyalkyl or —alk—NR$_7$R$_8$ radicals; or a heteroaromatic chosen from the pyridyl, pyrimidyl, thiazolyl and thienyl rings, it being possible for these heteroaromatics to be unsubstituted or substituted with a halogen atom or an alkyl, alkoxy, hydroxyl, trifluoromethyl, trifluoromethoxy, —CONR$_7$R$_8$ or hydroxyalkyl radical, $R_4$ represents —Het or Ar, $R_6$ represents a hydroxyalkyl or alkyl radical, $R_7$ and $R_8$, which are identical or different, represent a hydrogen atom or an alkyl radical or alternatively $R_7$ and $R_8$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, Ar represents a phenyl or naphthyl radical, these different radicals being optionally substituted with one or more halogen atoms or alkyl, alkoxy, —CO—alk, cyano, —CONR$_{13}$R$_{14}$, —alk—NR$_{15}$R$_{16}$, —NR$_{15}$R$_{16}$, CF$_3$, OCF$_3$, SO$_2$NH$_2$, hydroxyl or hydroxyalkyl radicals, Het represents a 3- to 10-membered unsaturated or saturated mono- or bicyclic heterocycle containing one or more heteroatoms chosen from oxygen, sulfur and nitrogen optionally substituted with one or more halogen atoms or alkyl, alkoxy, oxo or hydroxyl radicals, and, more particularly, Het represents a heterocycle chosen from benzimidazole, benzoxazole, benzothiazole, benzothiophene, thiophene, quinazoline, quinoxaline, quinoline, pyrrole, pyridine, imidazole, indole, isoquinoline, thiazole, thiadiazole, furan, tetrahydroisoquinoline and tetrahydroquinoline, these heterocycles being optionally substituted with one or more halogen atoms or alkyl, alkoxy, alkoxycarbonyl, oxo, hydroxyl, OCF$_3$ or CF$_3$ radicals, $R_{13}$ and $R_{14}$, which are identical or different, represent a hydrogen atom or an alkyl radical or alternatively $R_{13}$ and $R_{14}$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, $R_{15}$ and $R_{16}$, which are identical or different, represent a hydrogen atom or an alkyl radical or alternatively $R_{15}$ and $R_{16}$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals.

Among the preferred compounds, the following compounds may be mentioned:

N-{1-[bis(4-chlorophenyl)methyl]azetidin-3-yl}-N-(6-chloropyrid-2-yl)methylsulfonamide, N-{1-[bis(4-chlorophenyl)methyl]azetidin-3-yl}-N-(6-ethylpyrid-2-yl)methylsulfonamide, N-{1-[bis(4-chlorophenyl)methyl]azetidin-3-yl}-N-quinol-6-ylmethylsulfonamide, N-{1-[bis(4-chlorophenyl)methyl]azetidin-3-yl}-N-quinol-5-ylmethylsulfonamide N-{1-[bis(4-chlorophenyl)methyl]azetidin-3-yl}-N-isoquinol-5-ylmethylsulfonamide, N-{1-[bis(4-chlorophenyl)methyl]azetidin-3-yl}-N-pyrid-3-ylmethylsulfonamide, N-{1-[bis(4-chlorophenyl)methyl]azetidin-3-yl}-N-(1-oxide-pyrid-3-yl)methylsulfonamide, N-(1R,2S,4S)-bicyclo[2.2.1]hept-2-yl-N-{1-[bis(4-chlorophenyl)methyl]azetidin-3-yl}methylsulfonamide, N-(1R,2R,4S)-bicyclo[2.2.1]hept-2-yl-N-{1-[bis(4-chlorophenyl)methyl]azetidin-3-yl}methylsulfonamide, N-{1-[bis(4-chlorophenyl)methyl]azetidin-3-yl}-N-(3,5-difluorophenyl)methylsulfonamide, N-{1-[bis(4-chlorophenyl)methyl]azetidin-3-yl}-N-(thiazol-2-yl)methylsulfonamide, N-{1-[bis(4-chlorophenyl)methyl]azetidin-3-yl}-N-(3-methoxyphenyl)methylsulfonamide, N-{1-[bis(4-chlorophenyl)methyl]azetidin-3-yl}-N-(3-hydroxyphenyl)methylsulfonamide, N-{1-[bis(4-chlorophenyl)methyl]azetidin-3-yl}-N-(3-hydroxymethylphenyl)methylsulfonamide, Ethyl N-{1-[bis(4-chlorophenyl)methyl]azetidin-3-yl}-N-(methylsulfonyl)-3-aminobenzoate, N-{1-[bis(4-chlorophenyl)methyl]azetidin-3-yl}-N-(1-isobutylpiperid-4-yl)methylsulfonamide, N-benzyl-N-{1-[bis(4-chlorophenyl)methyl]azetidin-3-yl}amine, N-{-[bis(4-chlorophenyl)methyl]azetidin-3-yl}-N-(3,5-difluorobenzyl)amine, N-{1-[bis(4-chlorophenyl)methyl]azetidin-3-yl}-N-(3,5-difluorobenzyl)methylsulfonamide, N-{1-[bis(4-chlorophenyl)methyl]azetidin-3-yl}-N-(pyrid-3-ylmethyl)methylsulfonamide N-{1-[bis(4-fluorophenyl)methyl]azetidin-3-yl}-N-(3,5-difluorophenyl)methylsulfonamide, (RS)-N-{1-[(4-chlorophenyl)pyrid-3-ylmethyl]azetidin-3-yl}-N-(3,5-difluorophenyl)methylsulfonamide, (R)-N-{1-[(4-chlorophenyl)pyrid-3-ylmethyl]azetidin-3-yl}-N-(3,5-difluorophenyl)methylsulfonamide, (S)-N-{1-[(4-chlorophenyl)pyrid-3-ylmethyl]azetidin-3-yl}-N-(3,5-difluorophenyl)methylsulfonamide, (RS)-N-{1-[(4-chlorophenyl)pyrid-4-ylmethyl]azetidin-3-yl}-N-(3,5-difluoro phenyl)methylsulfonamide, (R)-N-{1-[4-chlorophenyl)pyrid-4-ylmethyl]azetidin-3-yl}-N-(3,5-difluorophenyl)methylsulfonamide, (S)-N-{1-[4-chlorophenyl)pyrid-4-ylmethyl]azetidin-3-yl}-N-(3,5-difluorophenyl)methylsulfonamide, (RS)-N-{1-[(4-chlorophenyl)pyrimidin-5-ylmethyl]-azetidin-3-yl}-N-(3,5-difluorophenyl)methylsulfonamide, (R)-N-{1-[(4-chlorophenyl)pyrimidin-5-ylmethyl]-azetidin-3-yl}-N-(3,5-difluorophenyl)methylsulfonamide, (S)-N-{1-[(4-chlorophenyl)pyrimidin-5-ylmethyl]-azetidin-3-yl}-N-(3,5-difluorophenyl)methylsulfonamide,
N-{1-[bis(4-chlorophenyl)methyl]azetidin-3-yl}-N-(3,5-difluorophenyl)benzylsulfonamide,
their optical isomers and their pharmaceutically acceptable salts.

The compounds of formula (I) for which $R_1$ represents the radical $-N(R_4)R_5$ in which $R_5$ is a hydrogen atom, a radical $-N(R_4)-CO-R_5$ or $-N(R_4)-SO_2R_6$, $R_4$ is a radical $-C(R_{11})(R_{12})-Ar$ or $'C(R_{11})(R_{12})-Het$ and $R_{12}$ is a hydrogen atom may be prepared according to the following reaction scheme:

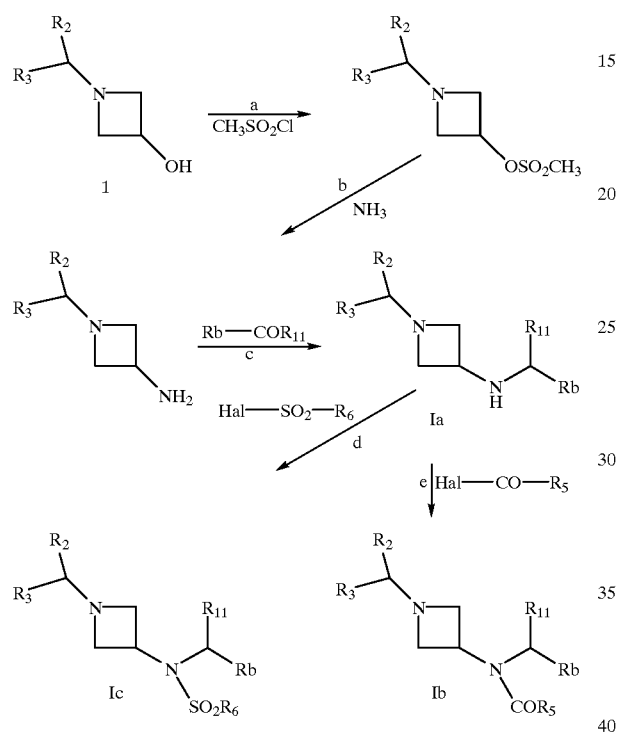

In these formulae, $R_2$, $R_3$, $R_6$ and $R_{11}$ have the same meanings as in formula (I), Rb represents an Ar or Het radical, Ar and Het having the same meanings as in formula (I) and Hal represents a halogen atom and preferably chlorine or bromine.

Step a is generally carried out in an inert solvent such as tetrahydrofuran, dioxane, a chlorinated solvent (for example dichloromethane or chloroform), at a temperature of between 15 and 30° C., in the presence of a base such as a trialkylamine (for example triethylamine or dipropylethylamine) or in pyridine, at a temperature of between 0 and 30° C.

Step b is preferably carried out in methanol, in an autoclave, at a temperature of between 50 and 70° C.

Step c is generally carried out in an inert solvent such as chlorinated solvent (for example dichloromethane), in the presence of sodium triacetoxyborohydride and acetic acid, at a temperature in the region of 20° C.

Steps d and e are generally carried out in an inert solvent such as tetrahydrofuran, dioxane, a chlorinated solvent (for example dichloromethane or chloroform), in the presence of an amine such as a trialkylamine (for example triethylamine), at a temperature of between 5° C. and 20° C.

The derivatives Rb—$COR_{11}$ are commercially available or may be obtained according to the methods described for example by R. C. LAROCK, Comprehensive Organic Transformations, VCH editor.

The derivatives Hal—$SO_2R_6$ are commercially available or may be obtained by halogenation of the corresponding sulfonic acids, in particular in situ in the presence of chlorosulfonyl isocyanate and alcohol, in a halogenated solvent (for example dichloromethane or chloroform).

The derivatives Hal—$COR_5$ are commercially available or may be prepared by halogenation of the corresponding carboxylic acids, in particular in situ in the presence of thionyl chloride in a halogenated solvent (for example dichloromethane or chloroform).

The azetidinols 1 may be obtained by application or adaptation of the methods described by KATRITZKY A. R. et al., J. Heterocycl. Chem., 271 (1994) or DAVE P. R., J. Org. Chem., 61, 5453 (1996) and in the examples. The procedure is generally carried out according to the following reaction scheme:

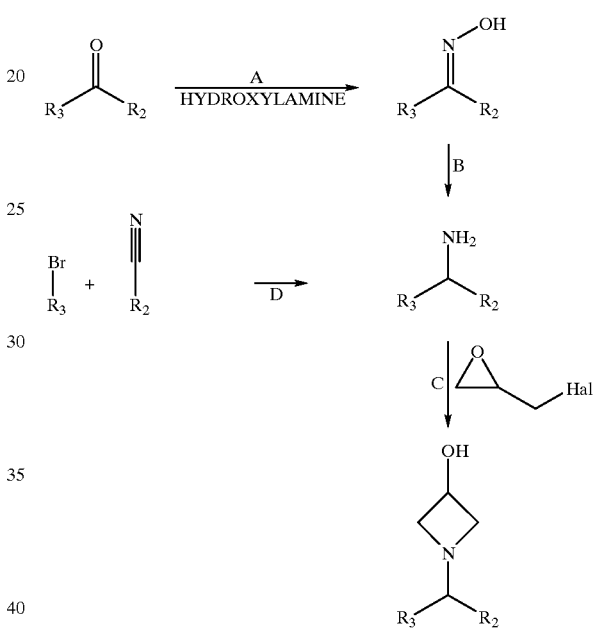

in these formulae, $R_2$ and $R_3$ have the same meanings as in formula (I) and Hal represents a chlorine or bromine atom.

In step A, the procedure is preferably carried out in an inert solvent such as a 1-4C aliphatic alcohol (for example ethanol or methanol), optionally in the presence of an alkali metal hydroxide, at the boiling point of the reaction medium.

In step B, the reduction is generally carried out, by means of lithium aluminum hydride, in tetrahydrofuran at the boiling point of the reaction medium.

In step C, the procedure is preferably carried out in an inert solvent such as a 1-4C aliphatic alcohol (for example ethanol or methanol), in the presence of sodium hydrogen carbonate, at a temperature of between 20° C. and the boiling point of the reaction medium.

In step D, the procedure is carried out according to the method described by GRISAR M. et al. in J. Med. Chem., 885 (1973). The magnesium compound of the brominated derivative is formed and then the nitrile is caused to react, in an ether such as ethyl ether, at a temperature of between 0° C. and the boiling point of the reaction medium. After hydrolysis with an alcohol, the intermediate imine is reduced in situ with sodium borohydride at a temperature of between 0° C. and the boiling point of the reaction medium.

The derivatives $R_2$—CO—$R_3$ are commercially available or may be obtained by application or adaptation of the methods described by KUNDER N. G. et al. J. Chem. Soc. Perkin Trans 1, 2815 (1997); MORENO-MARRAS M., Eur. J. Med. Chem., 23 (5) 477 (1988); SKINNER et al., J. Med. Chem., 14 (6) 546 (1971); HURN N. K., Tet. Lett., 36 (52) 9453 (1995); MEDICI A. et al., Tet. Lett., 24 (28) 2901 (1983); RIECKE R. D. et al., J. Org. Chem., 62 (20) 6921 (1997); KNABE J. et al., Arch. Pharm., 306 (9) 648 (1973); CONSONNI R. et al., J. Chem. Soc. Perkin Trans 1, 1809 (1996); FR-96-2481 and JP-94-261393.

The derivatives $R_3Br$ are commercially available or may be obtained by application or adaptation of the methods described by BRANDSMA L. et al., Synth. Comm., 20 (11) 1697 and 3153 (1990); LEMAIRE M. et al., Synth. Comm., 24 (1) 95 (1994); GODA H. et al., Synthesis, 9 849 (1992); BAEUERLE P. et al., J. Chem. Soc. Perkin Trans 2, 489 (1993).

The derivatives $R_2CN$ are commercially available or may be obtained by application or adaptation of the methods described by BOUYSSOU P. et al., J. Het. Chem., 29 (4) 895 (1992); SUZUKI N. et al., J. Chem. Soc. Chem. Comm., 1523 (1984); MARBURG S. et al., J. Het. Chem., 17 1333 (1980); PERCEC V. et al., J. Org. Chem., 60 (21) 6895 (1995).

The compounds of formula (I) for which $R_1$ represents a radical $-N(R_4)R_5$ may be prepared according to the following reaction scheme:

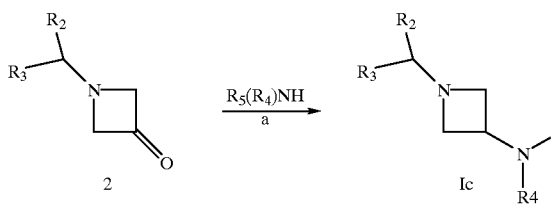

In these formulae, $R_2$, $R_3$, $R_4$ and $R_5$ have the same meanings as in formula (I).

This reaction is generally carried out in an inert solvent such as a chlorinated solvent (for example dichloromethane), in the presence of sodium triacetoxyborohydride and acetic acid, at a temperature in the region of 20° C.

The compounds $HN(R_4)R_5$ are commercially available or may be prepared according to conventional methods known to persons skilled in the art or by application or adaptation of the methods described by Park K. K. et al., J. Org. Chem., 60 (19) 6202 (1995); Kalir A. et al., J. Med. Chem., 12 (3) 473 (1969); Sarges R., J. Org. Chem., 40 (9) 1216 (1975); Zaugg H. E., J. Org. Chem., 33 (5) 2167 (1968); Med. Chem., 10, 128 (1967); J. Am. Chem. Soc., 2244 (1955); Chem. Ber., 106, 2890 (1973); Chem. Pharm. Bull., 16 (10) 1953 (1968); Bull. Soc. Chim. Fr., 835 (1962).

The azetidinones 2 may be obtained by oxidation of the corresponding acetidinols, preferably in dimethyl sulfoxide, by means of the sulfur trioxide-pyridine complex, at a temperature in the region of 20° C. or by means of dimethyl sulfoxide, in the presence of oxalyl chloride and triethylamine, at a temperature of between −70° C. and −50° C.

The compounds of formula (I) for which $R_1$ represents a radical $-N(R_4)COR_5$ or $-N(R_4)SO_2R_6$ may be prepared according to the following reaction scheme:

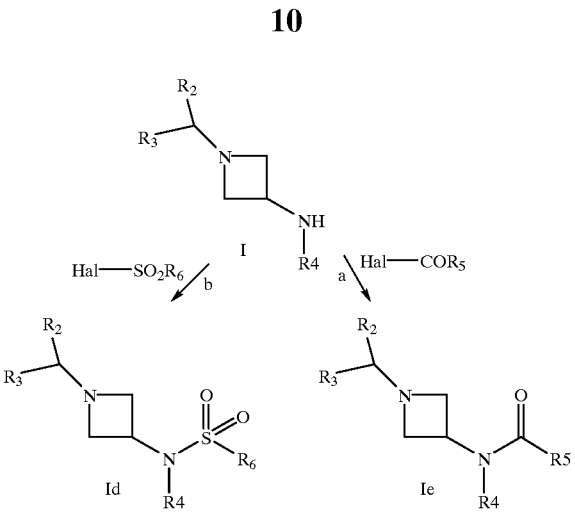

In these formulae, $R_2$, $R_3$, $R_4$, $R_5$ and $R_6$ have the same meanings as in formula (I) and Hal represents a halogen atom and preferably chlorine.

Steps a and b are generally carried out in an inert solvent such as tetrahydrofuran, dioxane, a chlorinated solvent (for example dichloromethane or chloroform), in the presence of an amine such as a trialkylamine (for example triethylamine), at a temperature of between 5° C. and 20° C.

The compounds of formula (I) for which $R_1$ represents a radical $-N(R_4)-SO_2-R_6$ for which $R_4$ is a Het or Ar radical may be prepared according to the following reaction scheme:

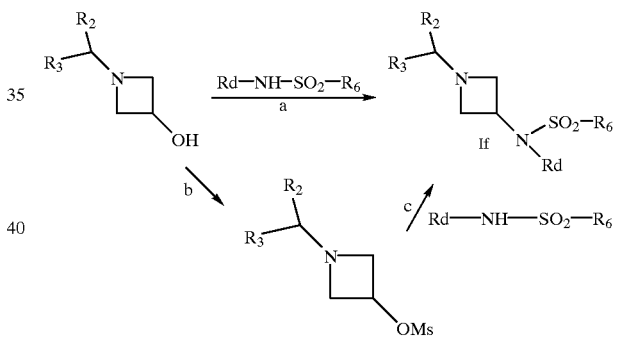

In these formulae, $R_2$, $R_3$ and $R_6$ have the same meanings as in formula (I), Rd represents an Ar or Het radical (Het and Ar having the same meanings as in formula (I)) and Ms represents a methylsulfonyloxy radical.

Step a is generally carried out in an inert solvent such as tetrahydrofuran, in the presence of triphenylphosphine and diethylazodicarboxylate, at a temperature of between 0° C. and the boiling point of the reaction medium.

Step b is generally carried out in an inert solvent such as tetrahydrofuran, dioxane, a chlorinated solvent (for example dichloromethane or chloroform), at a temperature of between 15° C. and 30° C., in the presence of a base such as a trialkylamine (for example triethylamine or dipropylethylamine) or in pyridine, at a temperature of between 0° C. and 30° C.

Step c is preferably carried out in an inert solvent such as dioxane in the presence of $CsCO_3$, at the reflux temperature of the reaction mixture.

The derivatives for which Rd represents an N-oxidized nitrogen-containing heterocycle may be reduced [lacuna] nonoxidized compound according to the method described by SANGHANEL E. et al., Synthesis 1375 (1996).

The derivatives $Rd-NH-SO_2R_6$ may be obtained according to the following reaction scheme:

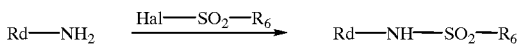

In these formulae, Hal represents a halogen atom, Rd represents a Het or Ar radical. The reaction is carried out in an inert solvent such as tetrahydrofuran, dioxane, a chlorinated solvent (for example dichloromethane or chloroform), at a temperature of between 15° C. and 30° C., in the presence of a base such as a trialkylamine (for example triethylamine or dipropylethylamine) or in pyridine, at a temperature of between 0° C. and 30° C.

The derivatives for which Rd represents an N-oxidized nitrogen-containing heterocycle may be obtained according to the method described by RHIE R., Heterocycles, 41 (2) 323 (1995).

The compounds of formula (I) may also be prepared according to the following reaction scheme:

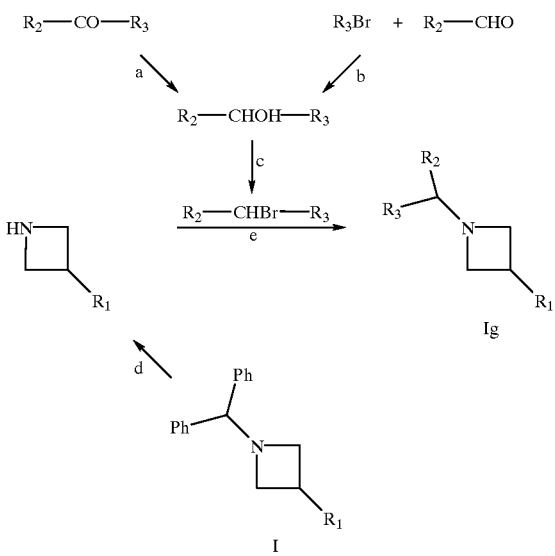

In these formulae, $R_1$, $R_2$ and $R_3$ have the same meanings as in formula (I) and Ph represents a phenyl.

Step a is generally carried out in an alcohol such as methanol, in the presence of sodium borohydride, at a temperature in the region of 20° C.

In step b, the magnesium compound of the brominated derivative is prepared and it is caused to react, in an inert solvent such as ethyl ether or tetrahydrofuran, at a temperature of between 0° C. and the boiling point of the reaction medium.

Step c is carried out by means of a halogenating agent such as hydrobromic acid, thionyl bromide, thionyl chloride, a mixture of triphenylphosphine and carbon tetrabromide or tetrachloride, in acetic acid or an inert solvent such as dichloromethane, chloroform, carbon tetrachloride or toluene, at a temperature of between 0° C. and the boiling point of the reaction medium.

Step d is carried out by means of hydrogen, in the presence of palladized charcoal, in an alcohol such as methanol, at a temperature in the region of 20° C.

Step e is carried out in an inert solvent such as acetonitrile, in the presence of an alkali metal carbonate (for example potassium carbonate) and potassium iodide, at a temperature of between 20° C. and the boiling point of the reaction medium.

The derivatives $R_3Br$ and the derivatives $R_2$—CHO are commercially available or may be obtained according to the methods described for example by R. C. LAROCK, Comprehensive Organic Transformations, VCH editor.

The compounds of formula (I) for which $R_1$ represents a radical —N($R_4$)—$SO_2$—$R_6$ for which $R_4$ is a 4-piperidyl radical optionally substituted on the nitrogen with an alkyl radical may also be prepared according to the following reaction scheme:

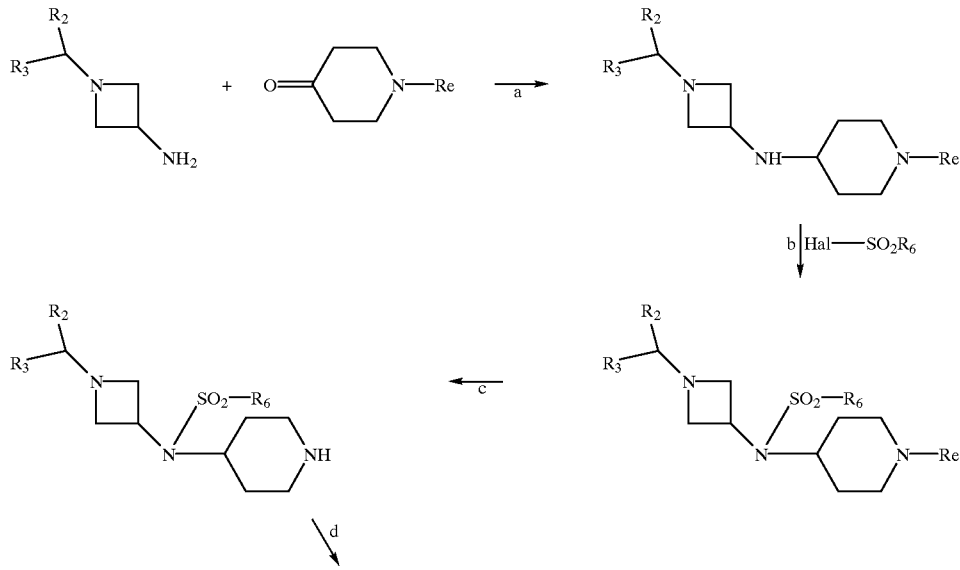

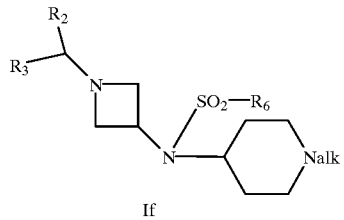

If

In these formulae, $R_2$, $R_3$ and $R_6$ have the same meanings as in formula (I), alk represents an alkyl radical and Re represents a tert-butylcarbonyloxy radical.

Step a is carried out in an inert solvent such as a chlorinated solvent (for example dichloromethane), in the presence of a hydride such as sodium triacetoxyborohydride and acetic acid, at a temperature of between 0° C. and the boiling point of the reaction medium.

Step b is generally carried out in an inert solvent such as tetrahydrofuran, dioxane, a chlorinated solvent (for example dichloromethane or chloroform), in the presence of an amine such as a trialkylamine (triethylamine for example), at a temperature of between 5° C. and 20° C.

Step c is carried out by means of hydrochloric acid, in dioxane, at a temperature of between 0° C. and the boiling point of the reaction medium.

Step d is carried out by any means known to persons skilled in the art for alkylating an amine without affecting the rest of the molecule. It is possible, for example, to use an alkyl halide, in the presence of an organic base such as triethylamine or an alkali metal hydroxide (for example sodium hydroxide or potassium hydroxide), optionally in the presence of tetrabutylammonium bromide, in an inert solvent such as dimethyl sulfoxide, dimethylformamide or pyridine, at a temperature of between 20 and 50° C.

The compounds of formula (I) for which $R_1$ represents a radical —N($R_4$)—$SO_2$—$R_6$ for which $R_4$ is a phenyl radical substituted with a 1-pyrrolidyl radical may also be prepared by the action of pyrrolidine on a corresponding compound of formula (I) for which $R_1$ represents a radical —N($R_4$)$SO_2R_6$ for which $R_4$ is a phenyl radical substituted with a halogen atom.

This reaction is preferably carried out in dimethyl sulfoxide, at a temperature of between 50 and 95° C.

It is understood for persons skilled in the art that, to carry out the processes according to the invention which are described above, it may be necessary to introduce groups protecting amino, hydroxyl and carboxyl functions in order to avoid side reactions. These groups are those which allow removal without affecting the rest of the molecule. As examples of groups protecting the amino function, there may be mentioned tert-butyl or methyl carbamates which may be regenerated using iodotrimethylsilane or allyl using palladium catalysts. As examples of groups protecting the hydroxyl function, there may be mentioned triethylsilyl and tert-butyldimethylsilyl which may be regenerated using tetrabutylammonium fluoride or alternatively asymmetric acetals (methoxymethyl or tetrahydropyranyl for example) with regeneration using hydrochloric acid. As groups protecting carboxyl functions, there may be mentioned esters (allyl or benzyl for example), oxazoles and 2-alkyl-1,3-oxazolines. Other protecting groups which can be used are described by GREENE T. W. et al., Protecting Groups in Organic Synthesis, second edition, 1991, John Wiley & Sons.

The compounds of formula (I) may be purified by the customary known methods, for example by crystallization, chromatography or extraction.

The enantiomers of the compounds of formula (I) may be obtained by resolution of the racemates for example by chromatography on a chiral column according to PIRCKLE W. H. et al., Asymmetric synthesis, Vol. 1, Academic Press (1983) or by formation of salts or by synthesis from chiral precursors. The diastereoisomers may be prepared according to known conventional methods (crystallization, chromatography or from chiral precursors).

The compounds of formula (I) may be optionally converted to addition salts with an inorganic or organic acid by the action of such an acid in an organic solvent such as an alcohol, a ketone, an ether or a chlorinated solvent. These salts also form part of the invention.

As examples of pharmaceutically acceptable salts, the following salts may be mentioned: benzenesulfonate, hydrobromide, hydrochloride, citrate, ethanesulfonate, fumarate, gluconate, iodate, isethionate, maleate, methane sulfonate, methylene-bis-b-oxynaphthoate, nitrate, oxalate, pamoate, phosphate, salicylate, succinate, sulfate, tartrate, theophyllineacetate and p-toluenesulfonate.

The compounds of formula (I) exhibit advantageous pharmacological properties. These compounds possess a high affinity for the cannabinoid receptors and particularly those of the CB1 type. They are CBI receptor antagonists and are therefore useful in the treatment and prevention of disorders affecting the central nervous system, the immune system, the cardiovascular or endocrine system, the respiratory system, the gastrointestinal apparatus and reproductive disorders (Hollister, Pharm. Rev.; 38, 1986, 1–20, Reny and Sinha, Prog. Drug Res., 36, 71–114 (1991), Consroe and Sandyk, in Marijuana/Cannabinoids, Neurobiology and Neurophysiology, 459, Murphy L. and Barthe A. Eds, CRC Press, 1992).

Accordingly, these compounds may be used for the treatment or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzheimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, in weaning from chronic treatments and alcohol or drug abuse (opioids, barbiturates, cannabis, cocaine, amphetamine, phencyclide, hallucinogens, benzodiazepines for example), as analgesics or potentiators of the analgesic activity of the narcotic and nonnarcotic drugs. They may also be used for the treatment or prevention of intestinal transit.

The affinity of the compounds of formula (I) for the cannabis receptors has been determined according to the method described by KUSTER J. E., STEVENSON J. I., WARD S. J., D'AMBRA T. E., HAYCOCK D. A. in J. Pharmacol. Exp. Ther., 264 1352–1363 (1993).

In this test, the $IC_{50}$ of the compounds of formula (I) is less than or equal to 1000 nM.

Their antagonist activity has been shown by means of the model of hypothermia induced by an agonist of the cannabis receptors (CP-55940) in mice, according to the method described by Pertwee R. G. in Marijuana, Harvey D. J. eds, 84 Oxford IRL Press, 263–277 (1985).

In this test, the $ED_{50}$ of the compounds of formula (I) is less than or equal to 50 mg/kg.

The compounds of formula (I) exhibit low toxicity. Their $LD_{50}$ is greater than 40 mg/kg by the subcutaneous route in mice.

The following examples illustrate the invention.

EXAMPLE 1

N-{1-[Bis-(4-chlorophenyl)methyl]azetidin-3-yl}-N-(6-chloropyrid-2-yl)methylsulfonamide may be prepared by carrying out the procedure in the following manner: 2.4 cm³ of diethyl azodicarboxylate and 1.44 g of triphenylphosphine are added, under argon, to a solution of 1.54 g of 1-[bis(4-chlorophenyl)methyl]-azetidin-3-ol and 1.22 g of N-(6-chloropyrid-2-yl)methylsulfonamide in 120 cm³ of anhydrous tetrahydrofuran. After stirring for 20 hours at 20° C., the reaction mixture is concentrated to dryness under reduced pressure (2.7 kPa). The residue is chromatographed on a silica gel column (particle size 0.040–0.063 mm, height 30 cm, diameter 4.5 cm), eluting under an argon pressure of 0.5 bar with a mixture of cyclohexane and ethyl acetate (80/20 by volume) and collecting 60-cm³ fractions. Fractions 6 to 9 are combined and concentrated to dryness under reduced pressure (2.7 kPa). 1.75 g of N-{1-[bis(4-chlorophenyl)methyl]azetidin-3-yl}-N-(6-chloropyrid-2-yl)-methylsulfonamide are obtained in the form of a white foam [$^1$H NMR spectrum (300 MHz, CDCl$_3$, δ in ppm): from 2.85 to 3.00 (mt: 2H); 2.91 (s: 3H); 3.57 (split t, J=7 and 2 Hz: 2H); 4.25 (s: 1H); 4.64 (mt: 1H); from 7.20 to 7.35 (mt: 9H); 7.36 (dd, J=8 and 1 Hz: 1H); 7.71 (t, J=8 Hz: 1H)].

1-[Bis(4-chlorophenyl)methyl]azetidin-3-ol may be prepared according to the procedure described by KATRITZKY A. R. et al., J. Heterocycl. Chem., 271 (1994), starting with 35.5 g of [bis(4-chlorophenyl)-methyl]amine hydrochloride and 11.0 cm³ of epichloro-hydrin. 9.0 g of 1-[bis(4-chlorophenyl)methyl]azetidin-3-ol are isolated.

Bis(4-chlorophenyl)methyl]amine hydrochloride may be prepared according to the method described by GRISAR M. et al., J. Med. Chem., 885 (1973).

N-(6-Chloropyrid-2-yl)methylsulfonamide may be prepared by carrying out the procedure in the following manner: 7.8 cm³ of methylsulfonyl chloride are poured dropwise, over 1 hour, into a solution, cooled to +5° C., of 2-amino-6-chloropyridine in 12.5 cm³ of pyridine. After returning to room temperature and stirring for 20 hours, the black reaction mixture is supplemented with 140 cm³ of water and extracted with 200 cm³ of dichloromethane. The organic phase is separated after settling, dried over magnesium sulfate, filtered and concentrated to dryness under reduced pressure (2.7 kPa). The oily residue obtained is chromatographed on a silica gel column (particle size 0.063–0.200 mm, height 30 cm, diameter 4 cm), eluting under an argon pressure of 0.5 bar with a mixture of cyclohexane and ethyl acetate (70/30 by volume) and collecting 60-cm³ fractions. Fractions 5 to 11 are combined and concentrated to dryness under reduced pressure (2.7 kPa). 17 g of N-(6-chloropyrid-2-yl)methylsulfonamide are obtained in the form of a yellow oil.

EXAMPLE 2

N-{1-[Bis(4-chlorophenyl)methyl]azetidin-3-yl}-N-(6-ethylpyrid-2-yl)methylsulfonamide may be prepared by carrying out the procedure as described in Example 1, starting with 0.61 g of 1-[bis(4-chlorophenyl)methyl]azetidin-3-ol, 0.40 g of N-(6-ethylpyrid-2-yl)methylsulfonamide, 50 cm³ of anhydrous tetrahydrofuran, 0.96 cm³ of diethyl azodicarboxylate and 0.577 g of triphenylphosphine. The crude product is chromatographed on a silica gel column (particle size 0.040–0.063 mm, height 20 cm, diameter 2 cm), eluting under an argon pressure of 0.5 bar with a mixture of cyclohexane and ethyl acetate (70/30 per volume) and collecting 30-cm³ fractions. Fractions 6 to 9 are combined and concentrated to dryness under reduced pressure (2.7 kPa). 0.3 g of an oil is obtained which is triturated in a mixture of 5 cm³ of diethyl ether and 5 cm³ of diisopropyl ether. The suspension is filtered, the solid drained and then dried under reduced pressure (2.7 kPa). 0.11 g of N-{1-[bis (4-chlorophenyl)methyl]-azetidin-3-yl}-N-(6-ethylpyrid-2-yl)methylsulfonamide is obtained in the form of a white solid [$^1$H NMR spectrum (300 MHz, CDCl$_3$, δ in ppm): 1.26 (t, J=7.5 Hz: 3H); 2.76 (q, J=7.5 Hz: 2H); from 2.85 to 2.95 (mt: 2H); 2.90 (s: 3H); 3.53 (split t, J=7 and 2 Hz: 2H); 4.22 (s: 1H); 4.69 (mt: 1H); 7.07 (d, J=7.5 Hz: 1H); from 7.15 to 7.30 (mt: 9H); 7.64 (t, J=7.5 Hz: 1H)].

N-(6-Ethylpyrid-2-yl)methylsulfonamide may be prepared by carrying out the procedure in the following manner: 1.56 cm³ of methylsulfonyl chloride are poured dropwise into a solution, cooled to +5° C., of 2.50 g of 2-amino-6-ethylpyridine in 2.50 cm³ of pyridine. After stirring for 20 hours at 20° C., the reaction mixture is supplemented with 8 cm³ of water and filtered. The filtrate is concentrated to dryness at 50° C. under reduced pressure (2.7 kPa). The residue is chromatographed on a silica gel column (particle size 0.040–0.063 mm, height 30 cm, diameter 4 cm), eluting under an argon pressure of 0.5 bar with 1.5 liters of dichloromethane and then with a mixture of dichloromethane and methanol (98/2 by volume) and collecting 60-cm³ fractions. Fractions 8 to 12 are combined and concentrated to dryness under reduced pressure (2.7 kPa). 2.8 g of N-(6-ethylpyrid-2-yl)methylsulfonamide are obtained in the form of a yellow oil.

EXAMPLE 3

N-{1-[Bis(4-chlorophenyl)methyl]azetidin-3-yl}-N-quinol-6-ylmethylsulfonamide may be prepared by carrying out the procedure in the following manner: 0.70 g of 1-[bis(4-chlorophenyl)methyl]azetidin-3-ol and 0.597 g of triphenylphosphine are added, under argon, to a solution of 0.50 g of N-quinol-6-ylmethylsulfonamide in 50 cm³ of anhydrous tetrahydrofuran and then 0.40 cm³ of diethyl azodicarboxylate is poured in. After stirring for 20 hours at 20° C., the reaction mixture is heated at the reflux temperature for 4 hours and then supplemented with 2.98 g of triphenylphosphine and 2.0 cm³ of diethyl azodicarboxylate. After stirring for 48 hours at 20° C., the mixture is concentrated to dryness under reduced pressure (2.7 kPa). The residue is taken up in 30 cm³ of diethyl ether, the suspension obtained is filtered and the filtrate is concentrated to dryness. A fraction of the residue obtained (0.90 g) is purified on a Bond Elut column of cation exchange sulfonic acid SCX resin (particle size 0.054 mm, height 4 cm, diameter 3 cm), eluting first with methanol and then with a 2 M solution of aqueous ammonia in methanol in order to elute the expected product, collecting 5-cm³ fractions. Fractions 16 to 19 are combined and concentrated to dryness under reduced pressure (2.7 kPa). 0.33 g of an oil is obtained which is stirred in 10 cm³ of diisopropyl ether. The resulting suspension is filtered. The filtrate, which is again filtered, gives, after 15 minutes, a solid which is dried at 50° C. under reduced pressure (2.7 kPa). 83 mg of N-{1-[bis(4-chlorophenyl) methyl]azetidin-3-yl}-N-quinol-6-ylmethylsulfonamide are obtained in the form of a white solid [$^1$H NMR spectrum (300 MHz, CDCl$_3$, δ in ppm): 2.87 (s: 3H); 2.89 (mt: 2H); 3.55 (split t, J=7 and 1 Hz: 2H); 4.18 (s: 1H); 4.69 (mt: 1H); from 7.15 to 7.30 (mt: 8H); 7.47 (dd, J=8.5 and 4 Hz: 1H); 7.58 (dd, J=9 and 2.5 Hz: 1H); 7.73 (d, J=2.5 Hz: 1H); 8.10 to 8.20 (mt: 2H); 8.97 (dd, J=4 and 1.5 Hz: 1H)]

N-Quinol-6-ylmethylsulfonamide may be prepared by carrying out the procedure in the following manner: 1.1 cm³ of methylsulfonyl chloride are poured dropwise, over 1 hour, into a solution, cooled to +3° C., of 1.98 g of 6-aminoquinoline in 1.75 cm³ of pyridine. After stirring for 20 hours at 20° C., the reaction mixture is supplemented with 10 cm³ of water and 50 cm³ of dichloromethane, and then filtered. The filtrate is separated after settling, the organic phase is dried over magnesium sulfate, and then filtered and concentrated to dryness under reduced pressure (2.7 kPa). 1.15 g of N-quinol-6-ylmethylsulfonamide are obtained in the form of a cream-yellow solid.

EXAMPLE 4

N-{1-[Bis(4-chlorophenyl)methyl]azetidin-3-yl}-N-quinol-6-ylmethylsulfonamide may be prepared by carrying out the procedure in the following manner: 0.70 g of 1-[bis(4-chlorophenyl)methyl]azetidin-3-ol and 0.597 g of triphenylphosphine are added, under argon, to a solution of 0.50 g of N-(quinol-5-yl)methylsulfonamide in 70 cm³ of anhydrous tetrahydrofuran and then 0.40 cm³ of diethyl azodicarboxylate and 0.45 g of 1,2-bis(diphenylphosphine) ethane are poured in. After stirring for 20 hours at 20° C., the reaction mixture is concentrated to dryness under reduced pressure (2.7 kPa). The residue is taken up in 70 cm³ of ethyl acetate, the resulting solution is washed with 30 cm³ of brine, dried over magnesium sulfate, filtered and then concentrated to dryness at 50° C. under reduced pressure (2.7 kPa). The violet oil obtained is purified by chromatography on a silica gel column (particle size 0.063–0.200 mm, height 35 cm, diameter 3.9 cm), eluting under an argon pressure of 0.5 bar with a mixture of cyclohexane and ethyl acetate (40/60 then 30/70 and 20/80 by volume) and collecting 50-cm³ fractions. Fractions 6 to 12 are combined and concentrated to dryness under reduced pressure (2.7 kPa). The residue is taken up in 15 cm³ of methanol, the resulting white suspension is filtered, the solid drained and then dried at 50° C. under reduced pressure (2.7 kPa). 0.35 g of N-{1-[bis(4-chlorophenyl)methyl]azetidin-3-yl}-N-quinol-5-ylmethylsulfonamide is obtained in the form of a white solid [$^1$H NMR spectrum (300 MHz, CDCl$_3$, δ in ppm): 2.60 (t, J=7 Hz: 1H); 2.84 (t, J=7 Hz: 1H); 2.99 (s: 3H); 3.36 (split t, J=7 and 2.5 Hz: 1H); 3.56 (split t, J=7 and 2.5 Hz: 1H); 4.01 (s: 1H); 4.85 (mt: 1H); from 7.10 to 7.25 (mt: 8H); 7.40 (dd, J=7.5 and 1 Hz: 1H); 7.54 (dd, J=8.5 and 4 Hz: 1H); 7.74 (dd, J=8 and 7.5 Hz: 1H); 8.20 (broad d, J=8 Hz: 1H); 8.54 (broad d, J=9 Hz: 1H); 8.99 (dd, J=4 and 1.5 Hz: 1H)].

N-(Quinol-5-yl)methylsulfonamide may be prepared by carrying out the procedure as described in Example 3, starting with 2.0 g of 5-aminoquinoline, 3.0 cm³ of pyridine, 1.1 cm³ of methylsulfonyl chloride. 2.47 g of N-(quinol-5-yl)methylsulfonamide are obtained in the form of a brown-yellow solid.

EXAMPLE 5

N-{1-[Bis(4-chlorophenyl)methyl]azetidin-3-yl}-N-isoquinol-5-ylmethylsulfonamide may be prepared by carrying out the procedure as described in Example 4, starting with 0.497 of N-(isoquinol-5-yl)methylsulfonamide, 70 cm³ of anhydrous tetrahydrofuran, 0.712 g of 1-[bis(4-chlorophenyl)methyl]azetidin-3-ol, 0.597 g of triphenylphosphine, 0.40 cm³ of diethyl azodicarboxylate and 0.45 g of 1,2-bis(diphenylphosphine)ethane. The crude brown oil obtained is purified by chromatography on a silica gel column (particle size 0.063–0.200 mm, height 38 cm, diameter 3 cm), eluting with a mixture of cyclohexane and ethyl acetate (30/70 by volume) and collecting 40-cm³ fractions. Fractions 8 to 23 are combined and concentrated to dryness under reduced pressure (2.7 kPa). The residue is stirred in 15 cm³ of diethyl ether, the suspension is filtered and the insoluble matter is chromatographed on a column of SCX resin (height 4 cm, diameter 3 cm), washing first with a mixture of methanol and dichloromethane (50/50 by volume) and then eluting with a 2 M solution of aqueous ammonia in methanol and collecting 20-cm³ fractions. Fractions 1 to 6 are combined and the white insoluble matter which appears is filtered, the solid is drained and then dried at 50° C. under reduced pressure (2.7 kPa). 0.169 g of N-{1-[bis(4-chlorophenyl)methyl]azetidin-3-yl}-N-isoquinol-5-ylmethylsulfonamide is obtained in the form of a white solid [$^1$H NMR spectrum (300 MHz, CDCl$_3$, δ in ppm): 2.64 (t, J=7 Hz: 1H); 2.81 (t, J=7 Hz: 1H); 2.99 (s: 3H); 3.36 (split t, J=7 and 2 Hz: 1H); 3.55 (split t, J=7 and 2 Hz: 1H); 4.02 (s: 1H); 4.86 (mt: 1H); from 7.10 to 7.25 (mt: 8H); 7.60 (dd, J=8 and 1 Hz: 1H); 7.66 (t, J=8 Hz: 1H); 7.93 (broad d, J=6 Hz: 1H); 8.06 (broad d, J=8 Hz: 1H); 8.66 (d, J=6 Hz: 1H); 9.32 (broad s: 1H)].

N-(Isoquinol-5-yl)methylsulfonamide may be prepared by carrying out the procedure as described in Example 4, starting with 2.0 g of 5-aminoisoquinoline, 3.0 cm³ of pyridine, 1.1 cm³ of methylsulfonyl chloride. 2.3 g of N-(isoquinol-5-yl)methylsulfonamide are obtained in the form of a beige solid.

EXAMPLE 6

N-{1-[Bis(4-chlorophenyl)methyl]azetidin-3-yl}-N-pyrid-3-ylmethylsulfonamide may be prepared by carrying out the procedure in the following manner: 0.042 cm³ of phosphorus trichloride is poured into a solution of 0.144 g of N-{1-[bis(4-chlorophenyl)methyl]azetidin-3-yl}-N-(1-oxide-pyrid-3-yl)methylsulfonamide in 5 cm³ of chloroform and then the mixture is heated to the reflux temperature. After stirring for 1 hour 30 minutes, the reaction mixture is allowed to return to room temperature and is then supplemented with 5 cm³ of 0.1 N hydrochloric acid, then stirred and separated after settling. The organic phase is diluted with 20 cm³ of chloroform, dried over magnesium sulfate, filtered and then concentrated to dryness under reduced pressure (2.7 kPa). The residue is chromatographed on a silica gel column (particle size 0.063–0.200 mm, height 9 cm, diameter 1.8 cm), eluting under an argon pressure of 0.1 bar with a mixture of dichloromethane and methanol (95/5 by volume) and collecting 15-cm³ fractions. Fractions 2 to 4 are combined and concentrated to dryness under reduced pressure (2.7 kPa). The residue is stirred with 15 cm³ of diethyl ether, the suspension is filtered, the solid is drained and then dried under reduced pressure (2.7 kPa). 35 mg of N-{1-[bis(4-chlorophenyl)methyl]azetidin-3-yl}-N-pyrid-3-ylmethylsulfonamide are obtained in the form of a cream-coloured solid [$^1$H NMR spectrum (300 MHz, CDCl$_3$, δ in ppm): from 2.80 to 2.95 (mt: 2H); 2.87 (s: 3H); 3.51 (split t, J=7 and 1.5 Hz: 2H); 4.18 (s: 1H); 4.65 (mt: 1H); from 7.15 to 7.35 (mt: 8H); 7.37 (broad dd, J=8 and 5 Hz: 1H); 7.64 (decoupled d, J=8 Hz: 1H); 8.52 (broad d, J=2 Hz: 1H); 8.61 (broad d, J=5 Hz: 1H)].

EXAMPLE 7

N-{1-[Bis(4-chlorophenyl)methyl]azetidin-3-yl}-N-(1-oxide-pyrid-3-yl)methylsulfonamide may be prepared by carrying out the procedure in the following manner: 0.16 cm$^3$ of diethyl azodicarboxylate and 0.226 g of triphenylphosphine are added, under argon, to a solution of 0.265 g of 1-[bis(4-chlorophenyl)methyl]azetidin-3-ol and 0.162 g of N-(1-oxide-pyrid-3-yl)methylsulfonamide, in 25 cm$^3$ of anhydrous tetrahydrofuran. After stirring for 20 hours at 20° C., and then for 24 hours at the reflux temperature, the reaction mixture is concentrated to dryness under reduced pressure (2.7 kPa). The residue is chromatographed on a silica gel column (particle size 0.063–0.2 mm, height 20 cm, diameter 1.5 cm), eluting under an argon pressure of 0.5 bar with a mixture of dichloromethane and methanol (98/2 by volume) and collecting 40-cm$^3$ fractions. Fractions 26 to 64 are combined and concentrated to dryness under reduced pressure (2.7 kPa). The residue is stirred in 10 cm$^3$ of diethyl ether, the suspension is filtered, the insoluble matter is drained and then dried under reduced pressure (2.7 kPa). 0.1 g of N-{1-[bis(4-chlorophenyl)methyl]azetidin-3-yl}-N-(1-oxide-pyrid-3-yl)methylsulfonamide is obtained in the form of a white solid [$^1$H NMR spectrum (400 MHz, (CD$_3$)$_2$SO d6, δ in ppm): 2.78 (t, J=7 Hz: 2H); 3.06 (s: 3H); 3.37 (t, J=7 Hz: 2H); 4.45 (s: 1H); 4.71 (mt: 1H); from 7.30 to 7.50 (mt: 10H); 8.21 (broad d, J=6.5 Hz: 1H); 8.27 (broad s: 1H)].

N-(1-Oxide-pyrid-3-yl)methylsulfonamide may be prepared by carrying out the procedure in the following manner: 7.1 g of 50–55% 3-chloroperoxybenzoic acid are added, in fractions, to a solution of 1.81 g of N-pyrid-3-ylmethylsulfonamide in 71 cm$^3$ of N,N-dimethylformamide and 3 cm$^3$ of methanol, followed by 0.56 cm$^3$ of 40% hydrofluoric acid. After stirring for 1 hour at 20° C., the reaction mixture is poured into 500 g of ice, stirred and then filtered. The filtrate is concentrated to dryness at 60° C. under reduced pressure (2.7 kPa). The residue is taken up in 50 cm$^3$ of a mixture of dichloromethane and methanol (98/2 by volume) and then filtered. The filtrate is chromatographed on a silica gel column (particle size 0.063–0.2 mm, height 27 cm, diameter 4 cm), eluting under an argon pressure of 0.5 bar with a mixture of dichloromethane and methanol (98/2, 97/3 and then 50/50 by volume) and collecting 60-cm$^3$ fractions. Fraction 62 is concentrated to dryness under reduced pressure (2.7 kPa). 0.96 g of N-(1-oxide-pyrid-3-yl)methylsulfonamide is obtained in the form of a yellowish solid.

N-Pyrid-3-ylmethylsulfonamide may be prepared by carrying out the procedure as described in Example 1, starting with 2 g of 3-aminopyridine, 5 cm$^3$ of pyridine and 1.8 cm$^3$ of methylsulfonyl chloride. The crude product obtained is stirred in 40 cm$^3$ of diethyl ether, the suspension is filtered and then the solid is drained and dried under reduced pressure (2.7 kPa). 2.47 g of N-pyrid-3-ylmethylsulfonamide are obtained in the form of a pinkish solid.

EXAMPLE 8

N-{1-[Bis(4-chlorophenyl)methyl]azetidin-3-yl}-N-cyclohexylmethylsulfonamide may be prepared by carrying out the procedure in the following manner: 0.4 cm$^3$ of methylsulfonyl chloride is added, with stirring, to a solution of 1.8 g of N-{1-[bis(4-chlorophenyl)methyl]azetidin-3-yl}-N-cyclohexylamine, 0.7 cm$^3$ of triethylamine and 20 mg of 4-dimethylaminopyridine in 25 cm$^3$ of dichloromethane. After stirring for 48 hours at 20° C., 20 cm$^3$ of dichloromethane and 20 cm$^3$ of water are added to the reaction mixture and it is stirred and separated after settling. The organic phase is dried over magnesium sulfate and concentrated at 50° C. under reduced pressure (2.7 kPa). The brown oily residue is chromatographed on a silica gel column (particle size 0.063–0.2 mm, height 20 cm, diameter 2.0 cm), eluting under an argon pressure of 0.1 bar with a mixture of dichloromethane and methanol (96/4 by volume) and collecting 10-cm$^3$ fractions. Fractions 2 to 4 and 5 to 10 are combined and concentrated to dryness under reduced pressure (2.7 kPa). The residue is chromatographed on a silica gel column (particle size 0.063–0.2 mm, height 30 cm, diameter 1.5 cm), eluting under an argon pressure of 0.1 bar with a mixture of cyclohexane and ethyl acetate (70/30 by volume) and collecting 5-cm$^3$ fractions. Fractions 7 to 10 are combined and concentrated to dryness under reduced pressure (2.7 kPa). 0.10 g of N-{1-[bis(4-chlorophenyl)methyl]azetidin-3-yl}-N-cyclohexylmethylsulfonamide is obtained in the form of a cream-coloured foam [$^1$H NMR spectrum (300 MHz, CDCl$_3$, δ in ppm): from 0.80 to 1.90 (mt: 10H); 2.82 (s: 3H); 3.36 (broad t, J=7.5 Hz: 2H); 3.46 (broad t, J=7.5 Hz: 2H); 3.59 (mt: 1H); 4.08 (mt: 1H); 4.42 (s: 1H); from 7.20 to 7.40 (mt: 8H)].

N-{1-[Bis(4-chlorophenyl)methyl]azetidin-3-yl}-N-cyclohexylamine may be prepared by carrying out the procedure in the following manner: 0.5 g of cyclohexylamine, 1 g of sodium triacetoxyborohydride and 0.3 cm$^3$ of 100% acetic acid are added to a solution of 1.5 g of 1-[bis(4-chlorophenyl)methyl]azetidin-3-one in 25 cm$^3$ of 1,-dichloroethane. After stirring for 20 hours at 20° C., 20 cm$^3$ of dichloromethane and 10 cm$^3$ of water are added to the reaction mixture, with stirring, and then the mixture is neutralized to pH 7 to 8 with a 1 N aqueous sodium hydroxide solution. The mixture is separated after settling, the organic phase is dried over magnesium sulfate and concentrated to dryness at 50° C. under reduced pressure (2.7 kPa). 1.8 g of N-{1-[bis(4-chlorophenyl)methyl]azetidin-3-yl}-N-cyclohexylamine are obtained in the form of a cream-coloured paste which will be used as it is in the next step.

1-[Bis(4-chlorophenyl)methyl]azetidin-3-one may be prepared according to the following procedure: a solution of 8.1 cm$^3$ of dimethyl sulfoxide in 17.6 cm$^3$ of dichloromethane is added to a solution of 5.0 cm$^3$ of oxalyl chloride in 73 cm$^3$ of dichloromethane cooled to –78° C. After 0.5 hour at –78° C., a solution of 16.0 g of 1-[bis(4-chlorophenyl)methyl]azetidin-3-ol, dissolved in 50 cm$^3$ of dichloromethane, is poured in. After 5 hours at –78° C., 26.6 cm$^3$ of triethylamine are added dropwise and the reaction mixture is allowed to return to room temperature. After 16 hours, the reaction mixture is washed with 4 times 200 cm$^3$ of water and then with 200 cm$^3$ of a saturated sodium chloride solution, dried over magnesium sulfate, filtered and concentrated to dryness under reduced pressure (2.7 kPa). The residue obtained is chromatographed on a silica gel column (particle size 0.04–0.06 mm, diameter 9.2 cm, height 21 cm), under an argon pressure of 0.5 bar with a mixture of ethyl acetate and cyclohexane (40/60 by volume) as eluents and collecting 200-cm$^3$ fractions. Fractions 15 to 25 are combined and then concentrated to dryness under reduced pressure (2.7 kPa). 8.9 g of 1-[bis(4-chlorophenyl)methyl]azetidin-3-one are obtained in the form of pale yellow crystals melting at 111° C.

EXAMPLE 9

N-{1-[Bis(4-chlorophenyl)methyl]azetidin-3-yl}-N-cyclopropylmethylsulfonamide may be prepared by carrying out the procedure as described in Example 8, starting with 1.6 g of N-{1-[bis(4-chlorophenyl)methyl]azetidin-3-yl}-N-cyclopropylamine, 25 cm³ of dichloromethane, 0.7 cm³ of triethylamine, 20 mg of 4-dimethylaminopyridine and 0.4 cm³ of methylsulfonyl chloride, while the mixture is stirred for 20 hours at 20° C. The crude product is chromatographed on a silica gel column (particle size 0.063–0.2 mm, height 30 cm, diameter 2.0 cm), eluting under an argon pressure of 0.1 bar with a mixture of dichloromethane and methanol (97/3 by volume) and collecting 10-cm³ fractions. Fractions 6 to 9 and 10 to 20 are combined and concentrated to dryness under reduced pressure (2.7 kPa). The residue obtained is chromatographed on a silica gel column (particle size 0.063–0.2 mm, height 30 cm, diameter 2.0 cm), eluting under an argon pressure of 0.1 bar with a mixture of cyclohexane and ethyl acetate (70/30 by volume) and collecting 10-cm³ fractions. Fractions 6 to 11 are combined and concentrated to dryness under reduced pressure (2.7 kPa). 0.14 g of N-{1-[bis(4-chlorophenyl)methyl]azetidin-3-yl}-N-cyclopropylmethylsulfonamide is obtained in the form of a cream-coloured foam [$^1$H NMR spectrum (300 MHz, CDCl$_3$, δ in ppm): 0.79 (mt: 2H); 0.95 (mt: 2H); 2.11 (mt: 1H); 2.84 (s: 3H); 3.17 (broad t, J=7 Hz: 2H); 3.50 (mt: 2H); 4.18 (mt: 1H); 4.29 (s: 1H); from 7.20 to 7.40 (mt: 8H)].

N-{1-[bis(4-chlorophenyl)methyl]azetidin-3-yl}-N-cyclopropylamine may be prepared by carrying out the procedure as described in Example 8, starting with 1.5 g of 1-[bis(4-chlorophenyl)methyl]azetidin-3-one, 25 cm³ of 1,2-dichloroethane, 0.37 cm³ of cyclopropylamine, 1 g of sodium triacetoxyborohydride and 0.3 cm³ of 100% acetic acid. 1.6 g of N-{1-[bis(4-chlorophenyl)methyl]azetidin-3-yl}-N-cyclopropylamine are obtained in the form of a brown oil which will be used as it is in the next step.

EXAMPLE 10

N-(1R,2S,4S)Bicyclo[2.2.1]hept-2-yl-N-{1-[bis(4-chlorophenyl)methyl]azetidin-3-yl}methylsulfonamide may be prepared by carrying out the procedure as described in Example 8, starting with 2.0 g of N-(1R,2S,4S)bicyclo[2.2.1]hept-2-yl-N-{1-[bis(4-chlorophenyl)methyl]azetidin-3-yl}amine, 25 cm³ of dichloromethane, 0.7 cm³ of triethylamine, 20 mg of 4-dimethylaminopyridine and 0.4 cm³ of methylsulfonyl chloride, with stirring for 20 hours. The brown oily residue is chromatographed on a silica gel column (particle size 0.063–0.2 mm, height 30 cm, diameter 2.0 cm), eluting under an argon pressure of 0.1 bar with a mixture of dichloromethane and methanol (97/3 by volume) and collecting 10-cm³ fractions. Fractions 6 to 18 are combined and concentrated to dryness under reduced pressure (2.7 kPa). The residue is chromatographed on a silica gel column (particle size 0.063–0.2 mm, height 30 cm, diameter 2.0 cm), eluting under an argon pressure of 0.1 bar with a mixture of cyclohexane and ethyl acetate (70/30 by volume) and collecting 10-cm³ fractions. Fractions 8 to 14 are combined and concentrated to dryness under reduced pressure (2.7 kPa). 0.70 g of N-(1R,2S,4S)bicyclo[2.2.1]hept-2-yl-N-{1-[bis(4-chlorophenyl)methyl]azetidin-3-yl}methylsulfonamide is obtained in the form of a cream-coloured foam [$^1$H NMR spectrum (300 MHz, CDCl$_3$, δ in ppm): from 1.20 to 1.75 (mt: 7H); 1.84 (broad t, J=12.5 Hz: 1H); 2.29 (mt: 1H); 2.35 (mt: 1H); 2.82 (s: 3H); from 3.35 to 3.55 (mt: 3H); 3.66 (mt: 1H); from 3.90 to 4.05 (mt: 2H); 4.51 (s: 1H); from 7.20 to 7.45 (mt: 8H)].

N-(1R,2S,4S)Bicyclo[2.2.1]hept-2-yl-N-{1-[bis(4-chlorophenyl)methyl]azetidin-3-yl}amine may be prepared by carrying out the procedure as described in Example 8, starting with 1.5 g of 1-[bis(4-chlorophenyl)methyl]azetidin-3-one, 25 cm³ of 1,2-dichloroethane, 1.5 g of (1R,2S,4S)bicyclo[2.2.1]hept-2-ylamine, 1 g of sodium triacetoxyborohydride and 0.3 cm³ of 100% acetic acid. 2 g of N-(1R,2S,4S)bicyclo[2.2.1]hept-2-yl-N-{1-[bis(4-chlorophenyl)methyl]azetidin-3-yl}amine are obtained in the form of a brown oil which will be used as it is in the next step.

EXAMPLE 11

N-(1R,2R,4S)Bicyclo[2.2.1]hept-2-yl-N-{1-[bis(4-chlorophenyl)methyl]azetidin-3-yl}methylsulfonamide may be prepared by carrying out the procedure as described in Example 8, starting with 1.8 g of N-(1R,2R,4S)bicyclo[2.2.1]hept-2-yl-N-{1-[bis(4-chlorophenyl)methyl]azetidin-3-yl}amine, 25 cm³ of dichloromethane, 0.7 cm³ of triethylamine, 20 mg of 4-dimethylaminopyridine and 0.4 cm³ of methylsulfonyl chloride, with stirring for 20 hours. The brown oily residue is chromatographed on a silica gel column (particle size 0.063–0.2 mm, height 30 cm, diameter 2.0 cm), eluting under an argon pressure of 0.1 bar with a mixture of cyclohexane and ethyl acetate (60/40 by volume) and collecting 10-cm³ fractions. Fractions 3 to 12 are combined and concentrated to dryness under reduced pressure (2.7 kPa). The residue is chromatographed on a silica gel column (particle size 0.063–0.2 mm, height 30 cm, diameter 2.0 cm), eluting under an argon pressure of 0.1 bar with a mixture of cyclohexane and ethyl acetate (70/30 by volume) and collecting 10-cm³ fractions. Fractions 4 to 10 are combined and concentrated to dryness under reduced pressure (2.7 kPa). 0.10 g of N-(1R,2R,4S)bicyclo[2.2.1]hept-2-yl-N-{1-[bis(4-chlorophenyl)methyl]azetidin-3-yl}methylsulfonamide is obtained in the form of a yellow foam [$^1$H NMR spectrum (300 MHz, CDCl$_3$, δ in ppm): from 1.00 to 1.85 (mt: 8H); 2.14 (mt: 1H); 2.33 (mt: 1H); 2.82 (s: 3H); from 3.40 to 3.60 (mt: 4H); 3.71 (broad dd, J=8 and 6 Hz: 1H); 4.10 (mt: 1H); 4.47 (s: 1H); from 7.20 to 7.40 (mt: 8H)].

N-(1R,2R,4S)Bicyclo[2.2.1]hept-2-yl-N-{1-[bis(4-chlorophenyl)methyl]azetidin-3-yl}amine may be prepared by carrying out the procedure as described in Example 8, starting with 1.5 g of 1-[bis(4-chlorophenyl)methyl]azetidin-3-one, 25 cm³ of 1,2-dichloroethane, 0.6 g of (1R,2R,4S)bicyclo[2.2.1]hept-2-ylamine, 1 g of sodium triacetoxyborohydride and 0.3 cm³ of 100% acetic acid. 1.8 g of N-(1R,2R,4S)bicyclo[2.2.1]hept-2-yl-N-{1-[bis(4-chlorophenyl)methyl]azetidin-3-yl}amine are obtained in the form of a cream-coloured paste which will be used as it is in the next step.

EXAMPLE 12

N-[(1-Benzhydryl)azetidin-3-yl]-N-phenylmethylsulfonamide may be prepared by carrying out the procedure in the following manner: 0.7 cm³ of methylsulfonyl chloride is poured into a solution of 2 g of 1-benzhydryl-3-anilinoazetidine in 40 cm³ of dichloromethane and then 1.34 cm³ of triethylamine are added. After stirring for 4 hours and 15 minutes at 20° C., the reaction mixture is washed with twice 20 cm³ of water, the organic phase is dried over magnesium sulfate and then concentrated to dryness at 50° C. under reduced pressure (2.7 kPa). The brown oil obtained is chromatographed on a silica gel column (particle size 0.063–0.2 mm, height 26 cm, diameter 3.6 cm), eluting under an argon pressure of 0.5 bar with a mixture of cyclohexane and ethyl acetate (70/30 by volume) and collecting 50-cm³ fractions. Fractions 10 to 15 are combined and concentrated to dryness under reduced pressure (2.7 kPa), the residue is triturated in diethyl ether, the suspension is filtered, the solid is drained and then dried under reduced pressure (2.7 kPa). 35 mg of N-[(1-benzhydryl)azetidin-3-yl]-N-phenylmethylsulfonamide are obtained in the form of a white solid [$^1$H NMR spectrum (300 MHz, (CD$_3$)$_2$SO d6 with addition of a few drops of CD$_3$COOD d4, δ in ppm): 2.72 (mt: 2H); 2.92 (s: 3H); 3.36 (mt: 2H); 4.32 (s: 1H); 4.73 (mt: 1H); from 7.10 to 7.45 (mt: 15H)].

1-Benzhydryl-3-anilinoazetidine may be prepared by carrying out the procedure as described in Example 8, starting with 5 g of 1-benzhydrylazetidin-3-one, 1.92 cm$^3$ of aniline, 74 cm$^3$ of 1,2-dichloroethane, 6.3 g of sodium triacetoxyborohydride and 1.2 cm$^3$ of 100% acetic acid. 8.81 g of 1-benzhydryl-3-anilinoazetidine are obtained in the form of a brown gum which will be used as it is in the next step.

EXAMPLE 13

N-{1-[Bis(4-chlorophenyl)methyl]azetidin-3-yl}-N-(3,5-difluorophenyl)methylsulfonamide may be prepared by carrying out the procedure in the following manner: 1.0 g of cesium carbonate is added to a mixture of 1.23 g of 1-[bis(4-chlorophenyl)methyl]azetidin-3-yl methylsulfonate and 0.66 g of N-(3,5-difluorophenyl)methylsulfonamide, in 25 cm$^3$ of dioxane. After stirring for 5 hours at the reflux temperature, and then for 20 hours at 20° C., the reaction mixture is supplemented with 50 cm$^3$ of diethyl ether and 30 cm$^3$ of brine, and is then stirred and separated after settling. The organic phase is dried over magnesium sulfate, filtered and then concentrated to dryness at 50° C. under reduced pressure (2.7 kPa). The orange-colored oil obtained is chromatographed on a silica gel column (particle size 0.040–0.063 mm, height 25 cm, diameter 2.0 cm), eluting under an argon pressure of 0.5 bar with a mixture of cyclohexane and ethyl acetate (65/35 by volume) and collecting 10-cm$^3$ fractions. Fractions 6 to 10 are combined and concentrated to dryness under reduced pressure (2.7 kPa). The residue is chromatographed on a silica gel column (particle size 0.040–0.063 mm, height 15 cm, diameter 1.0 cm), eluting under an argon pressure of 0.5 bar with a mixture of cyclohexane and ethyl acetate (65/35 by volume) and collecting 5-cm$^3$ fractions. Fraction 7 is concentrated to dryness under reduced pressure (2.7 kPa). 0.11 g of N-{1-[bis(4-chlorophenyl)methyl]azetidin-3-yl}-N-(3,5-difluorophenyl)methylsulfonamide is obtained in the form of a white powder [$^1$H NMR spectrum (300 MHz, CDCl$_3$, δ in ppm): 2.82 (s: 3H); 2.85 (mt: 2H); 3.52 (split t, J=7 and 2 Hz: 2H); 4.22 (s: 1H); 4.47 (mt: 1H); from 6.75 to 6.90 (mt: 3H); from 7.20 to 7.35 (mt: 8H)].
Method 2

0.78 cm$^3$ of diethyl azodicarboxylate and 1.31 g of triphenylphosphine are added, under argon, to a solution of 1.41 g of 1-[bis(4-chlorophenyl)methyl]azetidin-3-ol and 0.95 g of N-(3,5-difluorophenyl)methylsulfonamide in 100 cm$^3$ of anhydrous tetrahydrofuran. After stirring for 16 hours at 20° C., 300 cm$^3$ of ethyl acetate are added, the reaction mixture is washed twice with 100 cm$^3$ of water, dried over magnesium sulfate and concentrated to dryness under reduced pressure (2.7 kPa). The residue is chromatographed on a silica gel column (particle size 0.20–0.063 mm, height 50 cm, diameter 4 cm), eluting under an argon pressure of 0.6 bar with a mixture of cyclohexane and ethyl acetate (75/25 by volume) and collecting 125-cm$^3$ fractions. Fractions 6 to 12 are combined and concentrated to dryness under reduced pressure (2.7 kPa). 1.8 g of a solid are obtained, which solid is dissolved hot in an ethyl acetate/diisopropyl ether (15/2 by volume) mixture, cooled and diluted with 100 cm$^3$ of pentane in order to initiate the crystallization. After filtration and drying, 1.0 g of N-{1-[bis(4-chlorophenyl)methyl]azetidin-3-yl}-N-(3,5-difluorophenyl)methylsulfonamide is obtained in the form of white crystals melting at 154° C.

N-(3,5-Difluorophenyl)methylsulfonamide may be prepared by carrying out the procedure in the following manner: 2.0 cm$^3$ of methylsulfonyl chloride, 3.8 cm$^3$ of triethylamine and 20 mg of 4-dimethylaminopyridine are slowly added to a solution of 3.5 g of 3,5-difluoroaniline in 75 cm$^3$ of dichloromethane. After stirring for 20 hours at 20° C., the reaction mixture, supplemented with 20 cm$^3$ of dichloromethane and 20 cm$^3$ of water, is stirred and then separated after settling. The organic phase is dried over magnesium sulfate, filtered and then concentrated to dryness under reduced pressure (2.7 kPa). The residue is chromatographed on a silica gel column (particle size 0.063–0.200 mm, height 20 cm, diameter 2.0 cm), eluting under an argon pressure of 0.1 bar with dichloromethane and collecting 25-cm$^3$ fractions. Fractions 14 to 20 are combined and concentrated to dryness under reduced pressure (2.7 kPa). 0.66 g of N-(3,5-difluorophenyl)methylsulfonamide is obtained in the form of a white powder.

1-[Bis(4-chlorophenyl)methyl]azetidin-3-yl methyl sulfonate may be prepared by carrying out the procedure in the following manner: 3.5 cm$^3$ of methylsulfonyl chloride are added, under argon and over 10 minutes, to a solution of 12 g of 1-[bis(4-chloro-phenyl)methyl]azetidin-3-ol in 200 cm$^3$ dichloro-methane, then the mixture is cooled to +5° C. and 3.8 cm$^3$ of pyridine are poured in over 10 minutes. After stirring for 30 minutes at +5° C. and then for 20 hours at 20° C., the reaction mixture is diluted with 100 cm$^3$ of water and 100 cm$^3$ of dichloromethane. The mixture, which is first filtered, is separated after settling. The organic phase is washed with water, then dried over magnesium sulfate, filtered and concentrated to dryness under reduced pressure (2.7 kPa). The oil obtained is chromatographed on a silica gel column (particle size 0.063–0.200 mm, height 40 cm, diameter 3.0 cm), eluting under an argon pressure of 0.5 bar with a mixture of cyclohexane and ethyl acetate (70/30 by volume) and collecting 100-cm$^3$ fractions. Fractions 4 to 15 are combined and concentrated to dryness under reduced pressure (2.7 kPa). 6.8 g of 1-[bis(4-chlorophenyl)-methyl]azetidin-3-yl methyl sulfonate are obtained in the form of a yellow oil.

1-[Bis(4-chlorophenyl)methyl]azetidin-3-ol may be prepared according to the procedure described by KATRITZKY A. R. et al., J. Heterocycl. Chem., 271 (1994), starting with 35.5 g of [bis(4-chlorophenyl)-methyl]amine hydrochloride and 11.0 cm$^3$ of epichloro-hydrin. 9.0 g of 1-[bis(4-chloropheny)methyl]azetidin-3-ol are isolated.

[Bis(4-chlorophenly)methyl]amine hydrochloride may be prepared according to the method described by GRISAR M. et al., J. Med Chem., 885 (1973).

EXAMPLE 14

N-{1-[Bis(4-chlorophenyl)methyl]azetidin-3-yl}-N-(4,6-dimethylpyrimid-2-yl)methylsulfonamide may be prepared by carrying out the procedure as described in Example 13 (method 2), starting with 0.20 g of N-(4,6-dimethylpyrimid-2-yl)methylsulfonamide and 0.308 g of 1-[bis(4-chlorophenyl)methyl]azetidin-3-ol. After chromatography on a silica gel column (particle size 0.06–0.04 mm, height 50 cm, diameter 2 cm), eluting under an argon pressure of 0.6 bar with dichloromethane and then a mixture of dichloromethane +1% methanol and then a mixture of dichloromethane +2% methanol and collecting 200-cm$^3$ fractions, fractions 4 to 7 are combined and concentrated to dryness under reduced pressure (2.7 kPa). After crystallization from diisopropyl ether, filtration and drying, 0.20 g of N-{1-[bis(4-chlorophenyl)methyl]azetidin-3-yl}-N-(4,6-dimethylpyrimid-2-yl)methylsulfonamide is obtained in the form of a white solid [$^1$H NMR spectrum (300 MHz, CDCl$_3$, δ in ppm): 2.39 (s:6H); 2.89 (broad t, J×7.5 Hz:2H); 3.51 (s:3H); 3.77 (mt:2H); 4.27 (s:1H); 4.77 (mt:1H); 6.73 (s:1H); from 7.20 to 7.35 (mt:8H)].

N-(4,6-Dimethylpyrimid-2-yl)methylsulfonamide may be prepared by carrying out the procedure in the following manner: 1.4 cm$^3$ of triethylamine are added, at 0° C., to a mixture of 1.23 g of 2-amino-4,6-dimethylpyrimidine, 0.77 cm$^3$ of methylsulfonly chloride and 50 mg of 4-dimethylaminopyridine dissolved in 50 cm$^3$ of dichloromethane. After 16 hours at room temperature, the reaction medium is washed with twice 100 cm$^3$ of water, dried over magnesium sulfate, filtered and then evaporated to dryness under reduced pressure (2.7 kPa). 1.0 g of a yellow powder is obtained which is treated with 15 cm$^3$ of 10% sodium hydroxide at 100° C. for 1 hour. After cooling, the reaction mixture is extracted with twice 50 cm$^3$ of dichloromethane. The aqueous phase is acidified to pH=1 with 5 cm$^3$ of 10 N hydrochloric acid and extracted with twice 50 cm$^3$ of dichloromethane. The organic phases obtained are combined, washed with 50 cm$^3$ of water, dried over magnesium sulfate, filtered and concentrated. 0.20 g of N-(4,6-dimethylpyrimid-2-yl)-methylsulfonamide is obtained in the form of a yellow powder.

EXAMPLE 15

N-{1-[Bis(4-chlorophenyl)methyl]azetidin-3-yl}-N-(1,2,3,4-thiadiazol-2-yl)methylsulfonamide may be prepared by carrying out the procedure as described in Example 13 (method 2), from 0.10 g of N-(1,3,4-thiadiazol-2-yl)methylsulfonamide and 0.215 g of 1-[bis(4-chlorophenyl)methyl]azetidin-3-ol. After chromatography on a silica gel column (particle size 0.06–0.04 mm, height 25 cm, diameter 1 cm), eluting under an argon pressure of 0.8 bar with an ethyl acetate/cyclohexane 20/80 and then 40/60 by volume mixture and collecting 60-cm$^3$ fractions, fractions 26 to 31 are combined and concentrated to dryness under reduced pressure (2.7 kPa). After crystallization from dissopropyl ether, filtration and drying, 40 mg of N-{1-[bis(4-chlorophenyl)methyl]azetidin-3-yl}-N-(1,3,4-thiadiazol-2-yl)methylsulfonamide are obtained in the form of a white solid [$^1$H NMR spectrum (300 MHz, CDCl$_3$, δ in ppm): 3.01 (s:3H); 3.09 (split t, J=7 and 1.5 Hz:2H); 3.70 (split t, J=7 and 1.5 Hz:2H); 4.28 (s:1H); 4.76 (mt:1H); from 7.20 to 7.35 (mt:8H); 9.01 (s:1H)].

N-(1,3,4-Thiadiazol-2-yl)methylsulfonamide may be prepared by carrying out the procedure in the following manner: 1.5 cm$^3$ of methylsulfonyl chloride are added to a mixture of 2.02 g of 2-amino-1,3,4-thiadiazole in 10 cm$^3$ of pyridine. After 2 hours at room temperature, 60 cm$^3$ of water are added and the reaction medium is filtered. The aqueous phase collected is acidified to pH=2 with 1 N hydrochloric acid, extracted with twice 50 cm$^3$ of ethyl acetate, the organic phase washed with twice 50 cm$^3$ of water, dried over magnesium sulfate, filtered and then evaporated to dryness under reduced pressure (2.7 kPa). 0.1 g of a yellow powder is obtained.

EXAMPLE 16

N-{1-[Bis(4-chlorophenyl)methyl]azetidin-3-yl}-N-(thiadol-2-yl)methylsulfonamide may be prepared by carrying out the procedure as described in Example 15, starting with 0.50 g of N-(thiazol-2-yl)methyl-sulfonamide and 0.5 g of 1-[bis(4-chlorophyl)-methyl]azetidin-3-ol. After chromatography on a silica gel column (particle size 0.06–0.04 mm, height 60 cm, diameter 2 cm), eluting under an argon pressure of 0.9 bar with an ethyl acetate/cyclohexane 20/80 and then 40/60 by volume mixture and collecting 30-cm$^3$ fractions, fractions 9 to 12 are combined and concentrated to dryness under reduced pressure (2.7 kPa). After crystallization from diisopropyl ether, filtration and drying, 0.21 g of N-{1-[bis(4-chlorophenyl)methyl]azetidin-3-yl}-N-(thiazol-2-yl)methylsulfonamide is obtained in the form of a white solid [$^1$H NMR spectrum (300 MHz, CDCl$_3$, δ in ppm): from 2.95 to 3.10 (mt:2H); 3.00 (s:3H); 3.59 (mt:2H); 4.22 (broad s:1H); 4.69 (mt:1H); from 7.20 to 7.35 (mt:9H); 7.60 (mt:1H)].

N-(Thiazol-2-yl)methylsulfonamide may be prepared by carrying out the procedure in the following manner: 1.15 g of methylsulfonyl chloride are added to a mixture of 1.0 g of 2-aminothiazole in 5 cm$^3$ of pyridine. After 2 hours at room temperature, 20 cm$^3$ of water are added, the reaction medium is filtered and the solid collected (0.35 g). The aqueous phase collected is acidified to pH=2 with 1 N hydrochloric acid, extracted with twice 40 cm$^3$ of ethyl acetate, the organic phase washed with twice 30 cm$^3$ of water, dried over magnesium sulfate, filtered and then evaporated to dryness under reduced pressure (2.7 kPa). 0.15 g of a white solid is obtained which has spectral characteristics similar to the filtered solid corresponding to an N-(thiazol-2-yl)methylsulfonamide and N-(thiazol-2-yl)di(methylsulfonyl)imide mixture which is used as it is for the next step.

EXAMPLE 17

N-{1-[Bis(4-chlorophenyl)methyl]azetidin-3-yl}-N-(3-hydroxyphenyl)methylsulfonamide may be prepared by carrying out the procedure in the following manner: 7.63 cm$^3$ of a 1 M boron tribromide solution are added dropwise at 2° C. to a mixture of 0.5 g of N-{1-[bis(4-chlorophenyl)methyl]azetidin-3-yl}-N-(3-methoxy-phenyl)methylsulfonamide in 20 cm$^3$ of dichloromethane. After 20 hours at room temperature, the reaction medium is poured over ice and extracted with 60 cm$^3$ of dichloromethane. The organic phase [lacuna] washed with 3 times 80 cm$^3$ of water and then twice with 80 cm$^3$ of a saturated aqueous sodium chloride solution, dried over magnesium sulfate, filtered and then evaporated to dryness under reduced pressure (2.7 kPa). 0.33 g of a white foam is obtained which is taken up in acetonitrile, filtered and dried in order to obtain 0.20 g of a white solid [$^1$H NMR spectrum (300 MHz, CDCl$_3$, δ in ppm): 2.81 (s:3H); 2.86 (broad t, J=7.5 Hz:2H); 3.50 (broad t, J=7.5 Hz:2H); 4.20 (s:1H); 4.53 (mt:1H); 5.36 (unresolved complex: 1H); from 6.70 to 6.85 (mt: 3H) from 7.15 to 7.35 (mt: 9H)].

EXAMPLE 18

N-{1-[Bis(4-chlorophenyl)methyl]azetidin-3-yl}-N-(3-methoxyphenyl)methylsulfonamide may be prepared by carrying out the procedure as described in Example 15, starting with 1.58 g of N-(3-methoxyphenyl)methylsulfonamide and 2.0 g of 1-[bis(4-chlorophenyl)methyl]azetidin-3-ol. After chromatography on a silica gel column (particle size 0.06–0.04 mm, height 24 cm, diameter 7.8 cm), eluting under an argon pressure of 0.7 bar with an ethyl acetate/cyclohexane 50/50 and then 40/60 by volume mixture and collecting 100-cm$^3$ fractions, fractions 7 to 10 are combined and concentrated to dryness under reduced pressure (2.7 kPa). (2.05 g). After crystallization from diisopropyl ether, filtration and drying, 0.21 g of N-{1-[bis(4-chlorophenyl) methyl]azetidin-3-yl}-N-(3-methoxyphenyl) methylsulfonamide is obtained.

N-(3-Methoxyphenyl)methylsulfonamide may be prepared by carrying out the procedure in the following manner: 3.14 cm³ of methylsulfonyl chloride are added at 3° C. to a mixture of 5.0 g of 3-methoxyaniline in 150 cm³ of pyridine. After 20 hours at room temperature, 200 cm³ of water and 400 cm³ of ethyl acetate are added and the reaction medium is separated after settling. The organic phase is washed with 3 times 400 cm³ of water and 400 cm³ of a saturated sodium chloride solution, dried over magnesium sulfate, filtered and then evaporated to dryness under reduced pressure (2.7 kPa). After chromatography on a silica gel column (particle size 0.06–0.04 mm, height 23 cm, diameter 7.8 cm), eluting under an argon pressure of 0.7 bar with an ethyl acetate/cyclohexane 25/75 by volume mixture and collecting 100-cm³ fractions, fractions 24 to 36 are combined and concentrated to dryness under reduced pressure (2.7 kPa), 6.21 g of N-(3-methoxyphenyl) methylsulfonamide are obtained in the form of an orange-colored oil.

EXAMPLE 19

N-{1-[Bis(4-chloropheny)methyl]azetidin-3-yl}-N-(3-hydroxymethylphenyl)methylsulfonamide may be prepared by carrying out the procedure in the following manner: 1.46 cm³ of a 20% toluenic solution of diisopropylaluminum hydride are added dropwise at –50° C. to a mixture of 0.5 g of ethyl N-{1-[bis(4-chloro-phenyl)methyl]azetidin-3-yl}-N-(methylsulfonyl)-3-aminobenzoate in 20 cm³ of toluene. After 1.5 hours at 0° C. and 1.5 hours at 10° C., the reaction medium is cooled to 0° C. and 20 cm³ of water are added slowly. After filtration of the precipitate and extraction with ethyl acetate, the organic phase is washed with twice 80 cm³ of water and then 80 cm³ of a saturated aqueous sodium chloride solution, dried over magnesium sulfate, filtered and then evaporated to dryness under reduced pressure (2.7 kPa). 0.46 g of an oil is obtained which is chromatographed on a silica gel column (particle size 0.06–0.04 mm, height 16 cm, diameter 4 cm), eluting under an argon pressure of 0.7 bar with an ethyl acetate/cyclohexane 40/60 by volume mixture and collecting 20-cm³ fractions, fractions 72 to 76 are combined and concentrated to dryness under reduced pressure (2.7 kPa). 0.20 g of N-{1-[bis(4-chloropheny)methyl] azetidin-3-yl}-N-(3-hydroxymethylphenyl) methylsulfonamide is obtained in the form of a white solid [$^1$H NMR spectrum (300 MHz, CDCl$_3$, δ in ppm): 1.80 (mt:1H); 2.83 (s:3H); 2.87 (mt:2H); 3.52 (mt:2H); 4.21 (broad s:1 H); 4.60 (mt:1H); 4.74 (broad t, J=4 Hz:2H) from 7.10 to 7.45 (mt:12H)].

EXAMPLE 20

Ethyl N-{1-[bis(4-chlorophenyl)methyl]-azetidin-3-yl}-N-(methylsulfonyl)-3-aminobenzoate may be prepared by carrying out the procedure as described in Example 15, starting with 1.58 g of ethyl N-(methylsulfonyl)-3-aminobenzoate and 2.0 g of 1-[bis(4-chlorophenyl)methyl] azetidin-3-ol. After chromatography on a silica gel column (particle size 0.06–0.04 mm, height 24 cm, diameter 7.8 cm), eluting under an argon pressure of 0.7 bar with an ethyl acetate/cyclohexane 50/50 and then 40/60 by volume mixture and collecting 100-cm³ fractions, fractions 7 to 10 are combined and concentrated to dryness under reduced pressure (2.7 kPa) to give 2.0 g of a yellow oil.

Ethyl N-(methylsulfonyl)-3-aminobenzoate may be prepared by carrying out the procedure in the following manner: 2.35 cm³ of methylsulfonyl chloride are added at 3° C. to a mixture of 5.0 g of ethyl 3-aminobenzoate in 150 cm³ of pyridine. After 20 hours at room temperature, 200 cm³ of water and 400 cm³ of ethyl acetate are added and the reaction medium is separated after settling. The organic phase is washed with 3 times 400 cm³ of water and 400 cm³ of a saturated sodium chloride solution, dried over magnesium sulfate, filtered and then evaporated to dryness under reduced pressure (2.7 kPa). After chromatography on a silica gel column (particle size 0.06–0.04 mm, height 25 cm, diameter 7.8 cm), eluting under an argon pressure of 0.7 bar with an ethyl acetate/cyclohexane 25/75 by volume mixture and collecting 100-cm³ fractions, fractions 27 to 36 are combined and concentrated to dryness under reduced pressure (2.7 kPa), 5.24 g of ethyl N-(methylsulfonyl)-3-aminobenzoate are obtained in the form of an orange-colored oil.

EXAMPLE 21

N-{1-[Bis(4-chlorophenyl)methyl]azetidin-3-yl}-N-(1-isobutylpiperiod-4yl)methylsulfonamide may be prepared by carrying out the procedure in the following manner: 0.11 cm³ of isobutyraldehyde, 0.057 cm³ of 100% acetic acide and 320 mg of sodium triacetoxyborohydride are added to a solution of 0.47 g of N-{1-[bis(4-chlorophenyl)methyl] azetidin-3-yl}-N-(piperid-4-yl)methylsulfonamide in 20 cm³ of dichloromethane. After stirring for 20 hours at 20° C., the reaction mixture is supplemented with 50 cm³ of a saturated aqueous sodium hydrogen carbonate solution and separated after settling. The organic phase is dried over mangesium sulfate, filtered and concentrated to dryness under reduced pressure (2.7 kPa). The residue is purified by chromatography on a silica gel column (particle size 0.063–0.200 mm, height 20 cm, diameter 2 cm), eluting under an argon pressure of 0.5 bar with a mixture of cyclohexane and ethyl acetate (40/60 by volume) and collecting 30-cm³ fractions. Fractions 3 to 15 are combined and concentrated to dryness under reduced pressure (2.7 kPa). 0.22 g of N-{1-[bis(4-chloro-phenyl)methyl]azetidin-3-yl}-N-(1-isobutylpiperid-4 -yl)methylsulfonamide is obtained in the form of a white foam [$^1$H NMR spectrum (300 MHz, CDCl$_3$, δ in ppm): 0.87 (d, J=7 Hz:6H); from 1.60 to 1.90 (mt:5H); 1.93 (broad t, J=11.5 Hz:2H); 2.03 (d, J=7.5 Hz:2H); 2.84 (s, 3H); 2.89 (broad d, J=11.5 Hz:2H); 3,38 (broad t, J=7 Hz:2H); 3.47 (broad t, J=7 Hz:2H); 3.62 (mt:1H); 4.08 (mt:1H); 4.43 (s:1H); from 7.20 to 7.40 (mt:8H)].

N-{1-[Bis(4-chlorophenyl)methyl]azetidin-3-yl}-N-(piperid-4-yl)methylsulfonamide may be prepared by carying out the procedure in the following manner: 50 cm³ of a 6 N hydrochloric acid solution in dioxane is poured slowly into a solution of 19 g of N-{1-[bis(4-chlorophenyl)methyl] azetidin-3-yl}-N-(1-tert-butoxy-carbonylpiperid-4-yl) methylsulfonamide in 100 cm³ of dioxane. After stirring for 20 hours at 20° C., the reaction mixture is concentrated at 50° C. under reduced pressure (2.7 kPa). The residue is taken up in 200 cm³ of ethyl acetate and in 200 cm³ of water. The aqueous phase is alkalinized with a 4 N aqueous sodium hydroxide solution and then extracted with 200 cm³ of ethyl acetate. This organic phase is dried over magnesium sulfate, filtered and then concentrated to dryness under reduced pressure (2.7 kPa). 15.5 g of N-{1-[bis(4-chlorophenyl) methyl]azetidin-3-yl}-N-(piperid-4-yl) methylsulfonamide are obtained in the form of a cream-colored foam.

N-{1-[Bis(4-chlorophenyl)methyl]azetidin-3-yl}-N-(1-tert-butoxycarbonylpiperid-4-yl)methyl-sulfonylamide may be prepared by carrying out the procedure in the following manner: 4.60 cm³ of methyl-sulfonyl chloride are added slowly to a solution of 14.7 g of 4-{1-[bis(4-chlorophenyl)methyl]azetidin-3-ylamino}-(1-tert-butoxycarbonyl)piperidine in 250 cm³ of dichloromethane followed by 4.60 cm³ of triethylamine and 100 mg of 4-dimethylaminopyridine. After stirring for 20 hours at 20° C., the reaction mixture is supplemented with 200 cm³ of a saturated aqueous sodium hydrogen carbonate solution and then stirred for 30 minutes and separated after settling. The organic phase is dried over magnesium sulfate, filtered and then concentrated to dryness under reduced pressure (2.7 kPa). The foam obtained, taken up in 250 cm³ of dichloromethane, is again supplemented slowly with 4.60 cm³ of methylsulfonyl chloride and then with 4.60 cm³ of triethylamine and 100 mg of 4-dimethyl-aminopyridine. After stirring for 20 hours at 20° C., the mixture is supplemented with 200 cm³ of a saturated aqueous sodium hydrogen carbonate solution and then stirred for 30 minutes and separated after settling. The organic phase is dried over magnesium sulfate, filtered and then concentrated to dryness under reduced pressure (2.7 kPa). The residue is purified by chromatography on a silica gel column (particle size 0.063–0.200 mm, height 35 cm, diameter 5 cm), eluting under an argon pressure of 0.5 bar with a mixture of cyclohexane and ethyl acetate (70/30 by volume) and collecting 250-cm³ fractions. Fractions 4 to 18 are combined and concentrated to dryness under reduced pressure (2.7 kPa). 19 g of N-{1-[bis(4-chlorophenyl)methyl]azetidin-3-yl}-N-(1-tert-butoxycarbonylpiperid-4-yl)methylsulfonylamide are obtained in the form of a cream-colored foam which will be used as it is in the next step.

4-{1-[Bis(4-chlorophenyl)methyl]azetidin-3-ylamino}-(1-tert-butoxycarbonyl)piperidine may be prepared by carrying out the procedure in the following manner: 6.58 g of 1-tert-butoxycarbonylpiperidin-4-one are added to a solution of 9.22 g of 1-[bis(4-chlorophenyl)methyl]azetidin-3-ylamine in 300 cm³ of dichloromethane. 9.54 g of sodium triacetoxyborohydride are added, in two portions, to the mixture, cooled to +5° C., and then 1.72 cm³ of 100% acetic acid are poured in. After stirring for 20 hours at 20° C., the reaction mixture is supplemented slowly with 500 cm³ of a saturated aqueous sodium hydrogen carbonate solution and then thoroughly stirred and separated after settling. The organic phase is dried over magnesium sulfate, filtered and concentrated to dryness at 50° C. under reduced pressure (2.7 kPa). 15 g of 4-{1-[bis(4-chlorophenyl)methyl]azetidin-3-ylamino}-(1-tert-butoxycarbonyl)piperidine are obtained in the form of a cream-colored foam which will be used as it is in the next step.

EXAMPLE 22

N-Benzyl-N-{1-[bis(4-chlorophenyl)methyl]azetidin-3-yl}amine: 0.134 cm³ of benzaldehyde is added, at room temperature under an argon atmosphere, to a solution of 369 mg of 1-[bis(4-chlorophenyl)methyl]azetidin-3-ylamine in 15 cm³ of dichloromethane. The mixture is cooled to around 0° C., before gradually adding thereto 382 mg of sodium triacetoxyborohydride, and then 70 mm³ of acetic acid. After stirring for 16 hours at room temperature, the mixture is poured over 50 cm³ of a saturated aqueous sodium hydrogen carbonate solution and then extracted with twice 25 cm³ of dichloromethane. The combined organic phases are dried over magnesium sulfate, filtered and concentrated to dryness under reduced pressure (2.7 kPa). The residue obtained is purified by flash chromatography on silica gel [eluent: dichloromethane/methanol (95/5 by volume)]. 0.29 g of N-benzyl-N-{1-[bis(4-chlorophenyl)methyl]azetidin-3-yl}amine is obtained in the form of a colorless oil [¹H NMR spectrum (300 MHz, CDCl₃, δ ppm):2.71 (broad t, J=7 Hz,:2 H); 3.42 (mt:2 H); 3.49 (mt:1 H); 3.70 (s:2 H); 4.25 (s:1 H); from 7.20 to 7.40 (mt:13 H)].

1[Bis(4-chlorophenyl)methyl]azetidin-3-ylamine may be obtained in the following manner:400 cm³ of a mixture of methanol and liquid ammonia (50/50 by volume) are added to 27 g of 1-[bis(4-chlorophenyl)-methyl]azetidin-3-yl methylsulfonate contained in an autoclave previously cooled to around –60° C. The reaction medium is then stirred at 60° C. for 24 hours and then abandoned in the open air in order to allow the evaporation of the ammonia and finally concentrated under reduced pressure (2.7 kPa). The residue is taken up in 500 cm³ of a 0.37 N aqueous sodium hydroxide solution and extracted with four times 500 cm³ of ethyl ether. The combined organic phases are washed successively with twice 100 cm³ of distilled water and 100 cm³ of a saturated sodium chloride solution, dried over magnesium sulfate, filtered and concentrated under reduced pressure (2.7 kPa). The residue obtained is purified by flash chromatography on silica gel [eluent: dichloromethan/methanol (95/5 by volume)]. 14.2 g of 1-[bis(4-chlorophenyl)methyl]azetidin-3ylamine are obtained in the form of an oil which solidifies into a cream-colored solid.

EXAMPLE 23

N-Benzyl-N-{1-[bis(4-chlorophenyl)methyl]azetidin-3-yl}methylsulfonamide: 104 cm³ of triethylamine are added, at room temperature under an argon atmosphere, to a solution of 120 mg of N-benzyl-N-{1-[bis(4-chloropheny(methyl]azetidin-3-yl}amine in 5 cm³ of dichloromethane. The mixture is cooled to around 0° C. before adding thereto 46.4 mm³ of methylsulfonyl chloride, and then is is stirred at room temperature for 16 hours. The reaction mixture is diluted with 20 cm³ of dichloromethane and then is washed with twic 15 cm³ of distilled water. the organic phase is dried over magnesium sulfate, filtered and concentrated to dryness under reduced pressure (2.7 kPa), providing a lacquer which is crystallized by triturition in methanol. 42 mg of N-benzyl-N-{1-[bis(4-chlorophenyl)methyl]azetidin-3-yl}methylsulfonamide are thus obtained in the form of a cream-colored powder melting at 171° C.

EXAMPLE 24

N-{1-[Bis(4-chlorophenyl)methyl]azetidin-3-yl}-N-(3,5-difluorobenzyl)amine may be prepared as in Example 22, but using 188 mg of 3,5-difluoro-benzaldehyde and 369 mg of 1-[bis(4-chlorophenyl)-methyl]azetidin-3-ylamine and 382 mg of sodium triacetoxyborohydride, without purification by flash chromatography. 0.48 g of N-{1-[bis(4-chlorophenyl)-methyl]azetidin-3-yl}-N-(3,5-difluorobenzyl)amine is obtained in the form of a colorless oil [¹H NMR spectrum (300 MHz, CDCl₃, δ in ppm):2.73 (mt:2H); from 3.40 to 3.55 (mt:3H); 3.70 (s:2H); 4.26 (s:1H); 6.69 (tt, J=9 and 2 Hz:1H); 6.83 (mt:2H); from 7.20 to 7.35 (mt:8H)].

EXAMPLE 25

N-{1-[Bis(4-chlorophenyl)methyl]azetidin-3-yl}-N-(3,5-difluorobenzyl)methylsulfonamide 347 mm³ of triethylamine are added, at room temperature under an argon atmosphere, to a solution of 433 mg of N-{1-[bis(4-chlorophenyl)methyl]azetidin-3-yl}-N-(3,5-difluorobenzyl)amine in 30 cm³ of dichloro-methane. The mixture is cooled to around 0° C. before adding thereto a solution of 46.4 mm³ of methylsulfonyl chloride in 5 mm³ of dichloromethane, and then it is stirred at room temperature for 1 hour. The reaction mixture is diluted with 20 cm³ of dichloromethane and is then washed with twice 20 cm³ of distilled water. The organic phase is dried over magnesium sulfate, filtered and concentrated to dryness under reduced pressure (2.7 kPa). The residue is introduced into solution in methanol on a Bond Elut® SCX cartridge (10 g), eluting successively with methanol and with a 1 M solution of ammonia in methanol. The ammoniacal fractions are pooled and concentrated to dryness under reduced pressure (2.7 kPa). 0.44 g of N-{1-[bis(4-chloro-phenyl)methyl]azetidin-3-yl}-N-(3,5-difluorobenzyl)-methylsulfonamide is thus obtained in the form of a cream-colored foam [$^1$H NMR spectrum (300 MHz, CDCl$_3$, δ in ppm): 2.81 (s:3H); 3.02 (broad t, J=7.5 Hz: 2H); 3.38 (broad t, J=7.5 Hz:2H); 4.23 (s:1H); 4.40 (mt:1H); 4.54 (s:2H); 6.75 (tt, J=9 and 2 Hz:1H); 6.95 (mt:2H); 7.25 (mt:8H)].

EXAMPLE 26

N-{1-[Bis(4-chlorophenyl)methyl]azetidin-3-yl}-N-(3,5-difluorobenzyl)acetamide 1.6 cm³ of triethylamine are added, at room temperature under an argon atmosphere, to a solution of 2 g of N-{1-[bis(4-chlorophenyl)methyl]azetidin-3-yl}-N-(3,5-difluorobenzyl)amine in 75 cm³ of dichloro-methane. The mixture is cooled to around 0° C. before adding dropwise thereto 0.66 cm³ of acetyl chloride, and then it is stirred at room temperature for 16 hours. The reaction mixture is diluted with 50 cm³ of dichloromethane and is then washed with twice 20 cm³ of distilled water. The organic phase is dried over magnesium sulfate, filtered and concentrated to dryness under reduced pressure (2.7 kPa). The residue obtained is purified by flash chromatography on silica gel [eluent:dichloromethane/methanol (98/2 by volume)]. 1.2 g of N-{1-[bis(4-chlorophenyl)methyl]azetidin-3-yl}-N-(3,5-difluorobenzyl)acetamide are obtained in the form of a colorless oil [$^1$H NMR spectrum (300 MHz, CDCl$_3$, δ in ppm). A mixture of rotamers is observed. *2.06 and 2.14 (2s:3H in total); 2.97 (mt:2H); 3.43 (mt:2H); 4.20 and 4.25 (2s:1H in total); 4.54 and from 4.75 to 4.80 (mt:1H in total); 4.68 and 4.78 (broad 2s:2H in total); 6.70 (mt:3H); 7.24 (broad s :8H)].

EXAMPLE 27

N-{1-[Bis(4-chlorophenyl)methyl]azetidin-3-yl}-N-(pyrid-4-ylmethyl)methylsulfonamide 346 mm³ of triethylamine are added, at room temperature under an argon atmosphere, to a solution of 398 mg of N-{1-[bis(4-chlorophenyl)methyl]azetidin-3-yl}-N-(pyrid-4-ylmethyl)amine in 8 cm³ of dichloromethane. The mixture is cooled to around 0° C. before adding thereto 155 mm³ of methylsulfonyl choride, and then it is stirred at room temperature for 3 hours. The reaction mixture is diluted with 35 cm³ of dichloromethane and is then washed with twice 20 cm³ of distilled water. The organic phase is dried over magnesium sulfate, filtered and concentrated to dryness under reduced pressure (2.7 kPa). The residue obtained is purified by flash chromatography on silica gel [eluent:dichloromethane/methanol (97/3 by volume)]. 288 mg of N-{1-[bis(4-chlorophenyl)methyl]azetidin-3-yl}-N-(pyrid-4-ylmethyl)methylsulfonamide are obtained in the form of a cream-colored foam [$^1$H NMR spectrum (300 MHz, CDCl$_3$, δ in ppm):2.83 (s:3H); 3.02 (broad t, J=7.5 Hz: 2H); 3.40 (broad t, J=7.5 Hz: 2H); 4.23 (s: 1H); 4.43 (mt: 1H); 4.57 (s: 2H); from 7.20 to 7.35 (mt: 8H); 7.32 (broad d, J=5.5 Hz: 2H); 8.60 (broad d, J=5.5 Hz: 2H)].

EXAMPLE 28

N-{1-[Bis(4-chlorophenyl)methyl]azetidin-3-yl}-N-(pyrid-4-ylmethyl)amine may be prepared in the following manner: 0.126 cm³ of pyrid-4-ylcarboxaldehyde is added, at room temperature under an argon atmosphere, to a solution of 369 mg of 1-[bis(4-chlorophenyl)methyl]azetidin-3-ylamine in 15 cm³ of dichloromethane. The mixture is cooled to around 0° C., before gradually adding thereto 382 mg of sodium triacetoxyborohydride, and then 70 mm³ of acetic acid. After stirring for 72 hours at room temperature, the mixture is poured over 100 cm³ of a saturated aqueous sodium hydrogen carbonate solution and then extracted with twice 100 cm³ of dichloromethane. The combined organic phases are washed with 50 cm³ of distilled water, dried over magnesium sulfate, filtered and concentrated to dryness under reduced pressure (2.7 kPa). The residue is introduced into solution in 5 cm³ of methanol on a Bond Elut® SCX cartridge (10 g), eluting successively with 50 cm³ of methanol and with 60 cm³ of a 1 M solution of ammonia in methanol. The ammoniacal fractions are pooled and concentrated to dryness under reduced pressure (2.7 kPa). 0.48 g of N-{1-[bis(4-chlorophenyl)methyl]azetidin-3-yl}-N-(pyrid-4-ylmethyl)amine is thus obtained in the form of a colorless oil.

EXAMPLE 29

N-{1-[Bis(4-chlorophenyl)methyl]azetidin-3-yl}-N-(pyrid-3-ylmethyl)methylsulfonamide By carrying out the operation according to the procedure of Example 27, but starting with 380 mg of N-{1-[bis(4-chlorophenyl)methyl]azetidin-3-yl}-N-(pyrid-3-ylmethyl)amine, 319 mg of N-{1-[bis(4-chlorophenyl)methyl]azetidin-3-yl}-N-(pyrid-3-ylmethyl)methylsulfonamide are obtained in the form of a cream-colored foam [$^1$H NMR spectrum (300 MHz, CDCl$_3$, δ in ppm): 2.80 (s: 3H); 3.02 (split t, J=7 and 1.5 Hz: 2H); 3.38 (split t, J=7 and 1.5 Hz: 2H); 4.22 (s: 1H); 4.35 (mt: 1H); 4.56 (s: 2H); 7.23 (broad s: 8H); 7.31 (dd, J=8 and 5 Hz: 1H); 7.80 (broad d, J=8 Hz: 1H); 8.57 (dd, J=5 and 1.5 Hz: 1H); 8.63 (broad d, J=1.5 Hz: 1H)].

EXAMPLE 30

N-{1-[Bis(4-chlorophenyl)methyl]azetidin-3-yl}-N-(pyrid-3-ylmethyl)amine may be prepared as in Example 28, but starting with 0.124 cm³ of pyrid-3-ylcarboxaldehyde, 0.36 g of 1-[bis(4-chlorophenyl)methyl]azetidin-3-ylamine and 0.38 g of sodium triacetoxyborohydride. 0.44 g of N-{1-[bis(4-chlorophenyl)methyl]azetidin-3-yl}-N-(pyrid-3-ylmethyl)amine is thus obtained in the form of a colorless oil.

EXAMPLE 31

N-{1-[Bis(4-chlorophenyl)methyl]azetidin-3-yl}-N-(1,1-dioxo-1H-1λ$^6$-benzo[d]isothiazol-3-yl)amine 182 mg of 1,2-benzisothiazol-3-amine 1,1-dioxide and 326 mg of cesium carbonate are added to 386 mg of 1-[bis(4-chlorophenyl)methyl]azetidin-3-yl methylsulfonate in solution in 10 cm³ of dimethylformamide. The reaction medium is then stirred at 100° C. for 9 hours and then concentrated under reduced pressure (2.7 kPa). The residue is washed four times with 5 cm³ of boiling distilled water, disintegrated by stirring in 5 cm³ of distilled water at room temperature and then recovered by filtration and purified by flash chromatography on silica gel [eluent: dichloromethane/methanol (98/2 by volume)]. 53 mg of N-{1-[bis(4-chlorophenyl)methyl]azetidin-3-yl}-N-(1,1-dioxo-1H-1λ⁶-benzo[d]isothiazol-3-yl)amine are obtained in the form of a pasty product [[¹H NMR spectrum (300 MHz, CDCl₃, δ in ppm): 3.17 (mt: 2H); 3.61 (broad t, J=7.5 Hz: 2H); 4.37 (s: 1H); 4.75 (mt: 1H); from 6.30 to 6.40 (unresolved complex: 1H); from 7.20 to 7.35 (mt: 8H); 7.62 (broad d, J=7.5 Hz: 1H); 7.69 (broad t, J=7.5 Hz: 1H); 7.76 (broad t, J=7.5 Hz: 1H); 7.93 (broad d, J=7.5 Hz: 1H)].

1,2-Benzisothiazol-3-amine 1,1-dioxide may be prepared according to the method described by Stoss, P. et al., Chem. Ber. (1975), 108(12), 3855–63.

EXAMPLE 32

N-{1-[Bis(4-chlorophenyl)methyl]azetidin-3-yl}-N-(3,5-difluorophenyl)-N'-tert-butyloxycarbonylsulfamide may be prepared in the following manner: 0.048 cm³ of chlorosulfonyl isocyanate is added to a solution of 0.095 cm³ of tert-butyl alcohol in 2 cm³ of anhydrous dichloromethane, and after stirring for 2 minutes 0.21 g of N-{1-[bis(4-chlorophenyl)methyl]azetidin-3-yl}-(3,5-difluorophenyl)amine in 1.25 cm³ of anhydrous dichloromethane and then 0.084 cm³ of triethylamine are successively added. After stirring for 1 hour at a temperature in the region of 20° C., 2 cm³ of a saturated sodium bicarbonate solution are added with vigorous stirring. The reaction medium is separated after settling, dried over magnesium sulfate, filtered and then concentrated to dryness under reduced pressure (2.7 kPa). The residue obtained is chromatographed on a Varian cartridge (6 cm³) filled with 3 g of fine silica (0.040–0.063 mm), conditioned and then eluted with a petroleum ether-ethyl acetate mixture with the aid of a Duramat pump, collecting 2-cm³ fractions. Fractions 6 to 17 are combined and concentrated to dryness under reduced pressure (2.7 kPa) at 40° C. for 2 hours. 61 mg of N-{1-[bis(4-chlorophenyl)methyl]azetidin-3-yl}-N-(3,5-difluorophenyl)-N'-tert-butyloxycarbonylsulfamide are thus obtained in the form of a white foam [¹H NMR spectrum (400 MHz, CDCl₃, δ in ppm): 1.47 (s: 9H); 2.77 (broad t, J=8 Hz: 2H); 3.52 (mt: 2H); 4.19 (s: 1H); 5.06 (mt: 1H); from 6.75 to 6.90 (mt: 3H); from 7.15 to 7.35 (mt: 8H].

EXAMPLE 33

(RS)-N-{1-[(4-Chlorophenyl)pyridin-3-ylmethyl]azetidin-3-yl}-N-(3,5-difluorophenyl)methylsulfonamide may be obtained in the following manner: 0.2 g of potassium carbonate and 23 mg of potassium iodide are added to a mixture of 0.2 g of 3-[bromo-(4-chlorophenyl)methyl]pyridine and 0.22 g of N-azetidin-3-yl-N-(3,5-difluorophenyl)methylsulfonamide hydrochloride in 10 cm³ of acetonitrile, and then the mixture is heated under reflux for 3 hours. After adding 0.2 g of potassium carbonate, the mixture is heated under reflux for an additional 15 hours. After cooling to 21° C., the insoluble materials are removed by filtration and then the filtrate is concentrated to dryness at 40° C. under 2.7 kPa. 170 mg of a colorless lacquer are obtained, which lacquer is purified by chromatography on a silica cartridge (reference SIL-020-005, FlashPack, Jones Chromatography Limited, New Road, Hengoed, Mid Glamorgan, CF82 8AU, United Kingdom) eluting with a cyclohexane:ethyl acetate 1:1 mixture (6 cm³/min, 5-cm³ fractions). The fractions with an Rf=5/57 (cyclohexane:ethyl acetate 1:1, silica plate, Merck reference 1.05719, Merck KGaA, 64271 Darmstatd, Germany) are combined and concentrated under 2.7 kPa at 40° C. to give 100 mg of (RS)-N-{1-[(4-chlorophenyl)pyridin-3-ylmethyl]azetidin-3-yl}-(3,5-difluorophenyl)methylsulfonamide melting at 110° C. [¹H NMR spectrum (300 MHz, (CD₃)₂SO d6, δ in ppm): 2.77 (mt: 2H); 2.98 (s: 3H); 3.38 (mt: 2); 4.50 (s: 1H); 4.70 (mt: 1H); 7.11 (mt: 2H); from 7.20 to 7.40 (mt: 2H); 7.34 (d, J=8 Hz: 2H); 7.41 (d, J=8 Hz: 2H); 7.72 (broad d, J=8 Hz: 1H); 8.40 (dd, J=5 and 1.5 Hz: 1H); 8.58 (d, J=1.5 Hz: 1H)].

The two isomers of (RS)-N-{1-[(4-chlorophenyl)pyridin-3-ylmethyl]azetidin-3-yl}-N-(3,5-difluorophenyl)methanesulfonamide may be separated on a chiral stationary phase CHIRACEL OD.

First isomer: ¹H NMR spectrum (300 MHz, CDCl₃, δ in ppm): 2.82 (s: 3H); 2.87 (mt: 2H); 3.53 (mt: 2H); 4.29 (s: 1H); 4.47 (mt: 1H); 6.80 (mt: 3H); 7.19 (dd, J=8 and 5 Hz: 1H); from 7.20 to 7.35 (mt: 4H); 7.62 (broad d, J=8 Hz: 1H); 8.45 (broad d, J=5 Hz: 1H); 8.59 (broad s: 1H).

Second isomer: ¹H NMR spectrum (300 MHz, CDCl₃, δ in ppm): 2.82 (s: 3H); 2.87 (mt: 2H); 3.54 (mt: 2H); 4.29 (s: 1H); 4.48 (mt: 1H); 6.80 (mt: 3H); 7.19 (broad dd, J=8 and 5 Hz: 1H); from 7.25 to 7.35 (mt: 4H); 7.62 (dt, J=8 and 2 Hz: 1H); 8.46 (dd, J=5 and 2 Hz: 1H); 8.59 (broad d, J=2 Hz: 1H).

N-Azetidin-3-yl-N-(3,5-difluorophenyl)methylsulfonamide hydrochloride is obtained in the following manner: in a 500-cm³ hydrogenator, a solution of 1 g of N-(1-benzhydrylazetidin-3-yl)-N-(3,5-difluorophenyl)methylsulfonamide in a mixture of 2.5 cm³ of 1M hydrochloric acid and 0.41 cm³ of acetic acid is hydrogenated in the presence of 0.161 g of palladium hydroxide at a hydrogen pressure of 30 bar for 4 hours. The catalyst is removed by filtration on a celite bed and then the filtrate is concentrated to dryness at 40° C. under 2.7 kPa to give 630 mg of N-azetidin-3-yl-N-(3,5-difluorophenyl)methylsulfonamide, melting at 216° C.

N-(1-Benzhydrylazetidin-3-yl)-N-(3,5-difluorophenyl)methylsulfonamide may be obtained by carrying out the procedure as in Example 13 (method 2) in the following manner: 0.86 g of N-(3,5-difluorophenyl)methylsulfonamide, 3.28 g of triphenylphosphine and then 2 ml of diethyl azodicarboxylate are added successively to a solution of 2 g of 1-benzhydrylazetidin-3-ol in 100 cm³ of tetrahydrofuran. An increase in the temperature, which passes from 22° C. to 29° C., as well as the formation of a precipitate immediately following the addition of the diethyl azodicarboxylate are observed. After 20 h at 22° C., the precipitate is removed by filtration and the filtrate is concentrated to dryness at 40° C. under 2.7 kPa. The residue is triturated with 5 cm³ of methanol for 20 minutes at 21° C., providing 1.07 g of N-(1-benzhydrylazetidin-3-yl)-N-(3,5-difluorophenyl)methylsulfonamide in the form of a white amorphous solid.

1-Benzhydrylazetidin-3-ol may be prepared according to the procedure described by KATRITZKY A. R. et al., J. Heterocycl. Chem., 271 (1994).

3-[Bromo(4-chlorophenyl)methyl]pyridine is obtained in the following manner: 3.5 cm³ of a 48% solution of hydrobromic acid in acetic acid and 1 cm³ of acetyl bromide are added to 1.5 g of (4-chlorophenyl)pyridin-3-ylmethanol. The amber-colored mixture thus obtained is heated under reflux for 4 hours and then cooled to 20° C., concentrated to dryness at 40° C. under 2.7 kPa, giving 1.53 g of 3-[bromo(4-chlorophenyl)methyl]pyridine (Rf=75/90, 254 nm, Silica Plates, reference 1.05719, Merck KGaA, 64271 Darmstatd, Germany).

4-(Chlorophenyl)pyridin-3-ylmethanol is obtained in the following manner: 20 cm³ of a molar solution of 4-chlorophenylmagnesium bromide in ethyl ether are added to a solution of 3 g of 3-pyridine-carboxaldehyde in tetrahydrofuran at 5° C. After heating to 20° C., the mixture is allowed to react for 15 hours, with stirring. 20 cm³ of a saturated ammonium chloride solution are then added, followed by 20 cm³ of ethyl acetate. The mixture is separated after settling and the organic phases are extracted with an additional 20 cm³ of ethyl acetate. The organic extracts are combined, dried over magnesium sulfate and then concentrated to dryness at 40° C. under 2.7 kPa. The residue obtained is chromatographed on silica (Amicon, 20–45 μm, 500 g silica, column diameter 5 cm), eluting with a cyclohexane:ethyl acetate mixture from 80:20 to 50:50 under an argon pressure of 0.4 bar. The fractions containing the compound with an Rf=13/53 (Merck Silica Plates, reference 1.05719, Merck KGaA, 64271 Darmstatd, Germany) are combined and evaporated to dryness at 40° C. under 2.7 kPa to give 2.53 g of 4-chlorophenyl)pyridin-3-ylmethanol.

EXAMPLE 34

N-{1-[Bis(4-fluorophenyl)methyl]azetidin-3-yl}-N-(3,5-difluorophenyl)methylsulfonamide is obtained in the following manner: 0.36 g of potassium carbonate and 27 mg of potassium iodide are added to a mixture of 0.2 g of 4,4'-difluorobenzhydryl chloride and 0.26 g of N-azetidin-3-yl-N-(3,5-difluorophenyl)-hydrochloride in 10 cm³ of acetonitrile and then the mixture is heated under reflux for 3 hours. After cooling to 21° C., the insoluble materials are removed by filtration and then the filtrate is concentrated to dryness at 40° C. under 2.7 kPa. The residue is triturated with 30 cm³ of ethyl acetate and then the solid is removed by filtration. The filtrate is concentrated to dryness at 40° C. under 2.7 kPa and 90 mg of a pale yellow solid are obtained, which solid is purified by chromatography on BondElut SCX cartridge containing 2 g of graft silica (reference 1225-6019, Varian Associates, Inc. 24201 Frampton Avenue, Harbor City, Calif. 90710, USA) eluting with a 2 M solution of methanolic aqueous ammonia. The fractions with an Rf=16/82 (cyclohexane:ethyl acetate 7:3, silica plate, reference 1.05719, Merck KGaA, 64271 Darmstatd, Germany) are combined and concentrated under 2.7 kPa at 40° C. to give 243 mg of N-{1-[bis(4-fluorophenyl)methyl]azetidin-3-yl}-N-(3,5-difluorophenyl)methylsulfonamide melting at 98° C. [$^1$H NMR spectrum (300 MHz, (CD$_3$)$_2$SO d6, δ in ppm): 2.74 (broad t, J=7 Hz: 2H); 3.00 (s: 3H); 3.37 (broad t, J=7 Hz: 2H); 4.43 (s: 1H); 4.69 (mt: 1H); from 7.05 to 7.20 (mt: 6H); 7.28 (tt, J=9 and 2.5 Hz: 1H); 7.40 (mt: 4H)].

EXAMPLE 35

(RS)-N-{1-[(4-Chlorophenyl)pyridin-4-ylmethyl]azetidin-3-yl}-N-(3,5-difluorophenyl)methylsulfonamide may be obtained in the following manner: a mixture of about 100 mg of (4-pyridyl) (4-chlorophenyl)chloromethane, 143 mg of N-azetidin-3-yl-N-(3,5-difluorophenyl)methylsulfonamide hydrochloride, 17 mg of potassium iodide and 200 mg of potassium carbonate in 5 cm³ of acetonitrile is stirred for about 18 hours at a temperature in the region of 20° C. The reaction mixture is then heated under reflux for 3 hours, supplemented with 17 mg of potassium iodide and kept under reflux for an additional 2 hours. After cooling to a temperature in the region of 20° C., the reaction medium is filtered on sintered glass. The solid is rinsed with acetonitrile and then with twice 3 cm³ of ethyl acetate. The filtrates are concentrated to dryness under reduced pressure. 230 mg of a pale yellow paste are obtained, which paste is purified by preparative thin-layer chromatography on silica [4 Merck Kieselgel 60F254 preparative plates; 20×20 cm; thickness 0.5 mm], eluting with a methanol-dichloromethane (5–95 by volume) mixture. After elution of the zone corresponding to the desired product, filtration on sintered glass and then evaporation of the solvents under reduced pressure at a temperature in the region of 40° C., 12 mg of (RS)-N-{1-[(4-chlorophenyl)pyridin-4-ylmethyl]azetidin-3-yl}-N-(3,5-difluorophenyl)methylsulfonamide are obtained [$^1$H NMR spectrum (300 MHz, CDCl$_3$, δ in ppm): 2.82 (s: 3H); 2.96 (unresolved complex: 2H); from 3.50 to 3.80 (mt: 2H); 4.33 (unresolved complex: 1H); 4.54 (mt: 1H); 6.82 (mt: 3H); from 7.20 to 7.45 (mt: 6H); 8.53 (broad d, J=5.5 Hz: 2H)].

The two isomers of (RS)-N-{1-[(4-chlorophenyl)pyridin-4-ylmethyl]azetidin-3-yl}-N-(3,5-difluorophenyl)methanesulfonamide may be separated on a chiral stationary phase CHIRACEL OJ.

First isomer: $^1$H NMR spectrum (300 MHz, CDCl$_3$, δ in ppm): 2.83 (s: 3H); 2.87 (broad t, J=7.5 Hz: 2H); 3.51 (mt: 1H); 3.60 (mt: 1H); 4.24 (s: 1H); 4.50 (mt: 1H); 6.82 (mt: 3H); from 7.20 to 7.35 (mt: 6H); 8.50 (broad d, J=5.5 Hz: 2H).

Second isomer: $^1$H NMR spectrum (300 MHz, CDCl$_3$, δ in ppm): 2.83 (s: 3H); 2.88 (t, J=7.5 Hz; 2H); 3.51 (mt: 1H); 3.61 (mt: 1H); 4.25 (s: 1H); 4.51 (mt: 1H); 6.81 (mt: 3H); from 7.20 to 7.35 (mt: 6H); 8.50 (broad d, J=5.5 Hz: 2H).

(4-Pyridyl) (4-chlorophenyl)chloromethane may be prepared in the following manner: 0.0598 cm³ of thionyl choride is added to a suspension of 100 mg of (4-pyridyl) (4-chlorophenyl)methanol in 2 cm³ of toluene, cooled to a temperature in the region of 0° C. After 2 hours at a temperature in the region of 0° C. and 1 hour at a temperature in the region of 20° C., the reaction medium is concentrated under reduced pressure. About 100 mg of (4-pyridyl) (4-chlorophenyl)chloromethane are obtained in the form of a white solid.

(4-Pyridyl) (4-chlorophenyl)methanol may be prepared in the following manner: 348 mg of sodium tetraborohydride are added, at a temperature in the region of 20° C., to a solution of 2 g of 4-(4-chlorobenzoyl)pyridine in 160 cm³ of ethanol. After stirring for 2 hours at a temperature in the region of 20° C., 90 mg of sodium tetraborohydride are added. After about 1.5 hours at the same temperature, the reaction medium is diluted with 200 cm³ of dichloromethane and 200 cm³ of water. The pH of the aqueous phase is adjusted to a value of about 5 by addition of about 13 cm³ of a 1 N aqueous hydrochloric acid solution. After decantation, the aqueous phase is extracted with 3 times 100 cm³ of dichloromethane. The organic phases are combined, dried over magnesium sulfate, filtered and concentrated under reduced pressure. 2 g of (4-pyridyl) (4-chlorophenyl) methanol are thus obtained in the form of a white powder.

EXAMPLE 36

24.4 mg of a 75% dispersion of sodium hydride in mineral oil are added, at room temperature under an argon atmosphere, to a solution of 330 mg of {1-[bis(4-chlorophenyl)methyl]azetidin-3-yl}(3,5-difluorobenzyl) amine in 25 cm³ of tetrahydrofuran. The mixture is stirred at room temperature for 1 hour before adding thereto 59 mm³ of methyl chloroformate, and then the stirring is maintained for 18 hours under the same conditions. The reaction mixture is supplemented with 0.3 cm³ of distilled water and the tetrahydrofuran is expelled in a rotary evaporator. The residue obtained is extracted with dichloromethane, the organic phase is dried over magnesium sulfate, filtered and concentrated to dryness under reduced pressure (2.7 kPa). The residue obtained is purified by flash chromatography on silica gel [eluent: dichloromethane/methanol (97.5/2.5 by volume)]. 328 mg of methyl {1-[bis(4-chlorophenyl)methyl]azetidin-3-yl}-(3,5-difluorobenzyl)carbamate are obtained in the form of a colorless oil [$^1$H NMR spectrum (300 MHz, CDCl$_3$, δ in ppm): 2.97 (mt: 2H); 3.39 (mt: 2H); 3.71 (s: 3H); 4.24 (broad s: 1H); 4.45 (unresolved complex: 1H); 4.57 (s: 2H); from 6.65 to 6.80 (mt: 3H); from 7.15 to 7.30 (mt: 8H)].

EXAMPLE 37

(RS)-N-{1-[(4-Chlorophenyl)pyrimidin-5-ylmethyl]azetidin-3-yl}-N-(3,5-difluorophenyl)methylsulfonamide may be obtained by carrying out the procedure in Example 33, starting with 0.16 g of (RS)-5-[bromo-(4-chlorophenyl)methyl]pyrimidine hydrobromide, 0.131 g of N-azetidin-3-yl-N-(3,5-difluorophenyl)methanesulfonamide hydrochloride in 5 cm$^3$ of acetonitrile, 303 mg of potassium carbonate and 95 mg of potassium iodide; 26 mg of (RS)-N-{1-[(4-chlorophenyl)pyrimidin-5-yl-methyl]azetidin-3-yl}-N-(3,5-difluorophenyl)methylsulfonamide are thus obtained in the form of a yellow foam [$^1$H NMR spectrum (400 MHz, CDCl$_3$, δ in ppm): 2.83 (s: 3H); 2.91 (mt: 2H); 3.57 (mt: 2H); 4.31 (s: 1H); 4.50 (mt: 1H); from 6.75 to 6.90 (mt: 3H); 7.29 (s: 4H); 8.71 (s: 2H); 9.08 (s: 1H)].

The medicaments according to the invention consist of at least one compound of formula (I) or an isomer or a salt of such a compound, in the pure state or in the form of a composition in which it is combined with any other pharmaceutically compatible product which may be inert or physiologically active. The medicaments according to the invention may be used orally, parenterally, rectally or topically.

As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

Sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. Sterilization may be carried out in several ways, for example by asepticizing filtration, by incorporating sterilizing agents into the composition, by irradiation or by heating. They may also be prepared in the form of sterile solid compositions which may be dissolved at the time of use in sterile water or any other injectable sterile medium.

Compositions for rectal administration are suppositories or rectal capsules which contain, in addition to the active product, excipients such as cocoa butter, semisynthetic glycerides or polyethylene glycols.

Compositions for topical administration may be, for example, creams, lotions, collyria, collutoria, nasal drops or aerosols.

In human therapy, the compounds according to the invention are particularly useful for the treatment and/or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzheimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, intestinal transit disorders, in weaning from chronic treatments and alcohol or drug abuse (opioids, barbiturates, cannabis, cocaine, amphetamine, phencyclide, hallucinogens, benzodiazepines for example), as analgesics or potentiators of the analgesic activity of the narcotic and nonnarcotic drugs.

The doses depend on the desired effect, the duration of the treatment and the route of administration used; they are generally between 5 mg and 1000 mg per day orally for an adult with unit doses ranging from 1 mg to 250 mg of active substance.

In general, the doctor will determine the appropriate dosage depending on the age, weight and any other factors specific to the subject to be treated.

The following examples illustrate the compositions according to the invention:

EXAMPLE A

Gelatin capsules containing a dose of 50 mg of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a dose of 50 mg of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs 1 finished film-coated tablet containing 245 mg | |

EXAMPLE C

An injectable solution containing 10 mg of active product and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol, 95% | 0.4 ml |
| Sodium hydroxide | 24 mg |
| Propylene glycol | 1.6 ml |
| Water | qs 4 ml |

What is claimed is:

1. A pharmaceutical composition containing as active ingredient at least one compound of formula:

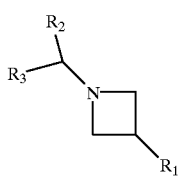

(I)

in which $R_1$ represents a radical selected from —N($R_4$)$R_5$, —N($R_4$)—CO—$R_5$, and —N($R_4$)—SO$_2$$R_6$, $R_2$ and $R_3$, which are identical or different, represent either A) an aromatic group selected from phenyl, naphthyl and indenyl, these aromatic groups being unsubstituted or substituted with one or more substituents selected from halogen, alkyl, alkoxy, formyl, hydroxyl, trifluoromethyl, trifluoromethoxy, —CO-alk, cyano, —COOH, COOalk, —CONR$_7$R$_8$, —CO—NH—NR$_9$R$_{10}$, alkylsulfanyl, alkylsulfinyl, alkylsulfonyl, alkylsulfanylalkyl, alkylsulfinylalkyl, alkylsulfonylalkyl, hydroxyalkyl and —alk—NR$_7$R$_8$ radicals; or B) a heteroaromatic group selected from benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidyl, quinolyl, 1,2,3,4-tetrahydroisoquinolyl, thiazolyl and thienyl rings, it being possible for these heteroaromatic groups to be unsubstituted or substituted with a substituent selected from halogen, alkyl, alkoxy, hydroxyl, trifluoromethyl, trifluoromethoxy, cyano, —COOH, COOalk, —CO—NH—NR$_9$R$_{10}$, —CONR$_7$R$_8$, —alk—NR$_9$R$_{10}$, alkylsulfanyl, alkylsulfinyl, alkylsulfonyl, alkylsulfanylalkyl, alkylsulfinylalkyl, alkylsulfonylalkyl and hydroxyalkyl, $R_4$ represents a radical selected from —C($R_{11}$)($R_{12}$)—Het, —Het, —(CR$_{11}$)($R_{12}$)—Ar, Ar, cycloalkyl and norbornyl, $R_5$ represents a radical selected from hydrogen, hydroxyalkyl, —alk—COOalk, —alk—CONR$_7$R$_8$, —alk—NR$_7$R$_8$, alkoxy, Ar, Het, —CH$_2$Ar, —CH$_2$Het and alkyl, said radical being optionally substituted with one or more halogens, $R_6$ represents a radical selected from hydroxyalkyl, —alk—COOalk, —alk—CONR$_7$R$_8$, —alk—NR$_7$R$_8$, alkoxy, Ar, Het, —CH$_2$Ar, —CH$_2$Het and alkyl, optionally substituted with 1 or more halogens, $R_7$ and $R_8$, which are identical or different, represent a radical selected from hydrogen and alkyl, or, alternatively, $R_7$ and $R_8$ together form with the nitrogen atom to which they are attached a 3- or 10-membered saturated mono- or bicyclic heterocycle, optionally containing another heteroatom selected from oxygen, sulfur and nitrogen and being optionally substituted with one or more alkyl radicals, $R_9$ and $R_{10}$, which are identical or different, represent a radical selected from hydrogen, alkyl, —COOalk, cycloalkyl, alkylcycloalkyl, —alk—O—alk and hydroxyalkyl or, alternatively, $R_9$ and $R_{10}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, —COalk, —COOalk, —CO—NHalk, —CS—NHalk, oxo, hydroxyalkyl, —alk—O—alk or —CO—NH$_2$ radicals, $R_{11}$ represents a radical selected from hydrogen, hydroxyalkyl, —alk—COOalk, —alk—CONR$_7$R$_8$, —alk—NR$_7$R$_8$, alkoxyalkyl, Ar, Het, —CH$_2$Ar, —CH$_2$Het and alkyl, optionally substituted with one or more halogen atoms, $R_{12}$ represents a radical selected from hydrogen, hydroxyalkyl, —alk—COOalk, —alk—CONR$_7$R$_8$, —alk—NR$_7$R$_8$, alkoxyalkyl and alkyl, optionally substituted with one or more halogen atoms, or alternatively $R_{11}$ and $R_{12}$ together form with the carbon atom to which they are attached a 3- to 10-membered saturated mono- or bicyclic ring, optionally containing another heteroatom selected from oxygen, sulfur and nitrogen and being optionally substituted with one or more alkyl radicals, Ar represents a phenyl, naphthyl or indenyl radical, these different radicals being optionally substituted with one or more halogen atoms or alkyl, alkoxy, —CO-alk, cyano, —COOH, —COOalk, —CONR$_{13}$R$_{14}$, —CO—NH—NR$_{15}$R$_{16}$, alkylsulfanyl, alkylsulfinyl, alkylsulfonyl, —alk—NR$_{15}$R$_{16}$, —NR$_{15}$R$_{16}$, alkylthioalkyl, formyl, CF$_3$, OCF$_3$, Het, —O—alk—NH—cycloalkyl, SO$_2$NH$_2$, hydroxyl, hydroxyalkyl, —NHCOalk, and NHCOOalk radicals or, on 2 adjacent carbon atoms, with dioxymethylene, Het represents a 3- or 10-membered unsaturated or saturated mono- or bicyclic heterocycle containing one or more heteroatoms selected from oxygen, sulfur and nitrogen optionally substituted with one or more halogen atoms or alkyl, alkoxy, alkoxycarbonyl, oxo or hydroxyl radicals, the nitrogen-containing heterocycles being optionally in their N-oxidized form, $R_{13}$ and $R_{14}$, which are identical or different, represent hydrogen or an alkyl radical or, alternatively, $R_{13}$ and $R_{14}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{15}$ and $R_{16}$, which are identical or different, represent hydrogen or an alkyl radical or, alternatively, $R_{15}$ and $R_{16}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, alk represents an alkyl or alkylene radical, the alkyl and alkylene radicals and portions and the alkoxy radicals and portions being in the form of straight or branched chains and containing 1 to 6 carbon atoms, and the cycloalkyl radicals containing 3 to 10 carbon atoms, the optical isomers of these compounds and their salts with a pharmaceutically acceptable inorganic or organic acid.

2. A pharmaceutical composition according to claim 1, wherein, in formula (I), Het is a heterocycle selected from benzimidazole, benzoxazole, benzothiazole, benzothiophene, cinnoline, thiophene, quinazoline, quinoxaline, quinoline, pyrazole, pyrrole, pyridine, imidazole, indole, isoquinoline, pyrimidine, thiazole, thiadiazole, piperidine, piperazine, triazole, furan, tetrahydroisoquinoline, and tetrahydroquinoline, these heterocycles being optionally substituted with one or more substituents selected from halogen, alkyl, alkoxy, alkoxycarbonyl, oxo, hydroxyl, $OCF_3$ and $CF_3$ radicals.

3. A pharmaceutical composition according to claim 1, wherein, in the compound of formula (I), $R_1$ represents a radical selected from $—N(R_4)R_5$ and $—N(R_4)—SO_2R_6$, $R_2$ represents either A) a phenyl which is unsubstituted or substituted with one or more substituents selected from halogen, alkyl, alkoxy, trifluoromethyl, trifluoromethoxy, —CO—alk, cyano, $—CONR_7R_8$, hydroxylalkyl and $—alk—NR_7R_8$; or B) a heteroaromatic ring selected from the pyridyl, pyrimidyl, thiazolyl and thienyl rings, it being possible for these heteroaromatic rings to be unsubstituted or substituted with a substituent selected from halogen, alkyl, alkoxy, hydroxyl, trifluoromethyl, trifluoromethoxy, $—CONR_7R_8$, $—alk—NR_9R_{10}$, alkylsulfanyl, alkylsulfinyl, alkylsulfonyl and hydroxyalkyl, $R_3$ represents either A) a phenyl which is unsubstituted or substituted with one or more substituents selected from halogen, alkyl, alkoxy, trifluoromethyl, trifluoromethoxy, —CO—alk, cyano, $—CONR_7R_8$, hydroxyalkyl and $—alk—NR_7R_8$; or B) a heteroaromatic ring selected from the pyridyl, pyrimidyl, thiazolyl and thienyl rings, it being possible for these heteroaromatic rings to be unsubstituted or substituted with a substituent selected from halogen, alkyl, alkoxy hydroxyl, trifluoromethyl, trifluoromethoxy, $—CONR_7R_8$, $—alk—NR_9R_{10}$, alkylsulfanyl, alkylsulfinyl, alkylsulfonyl and hydroxyalkyl, $R_4$ represents a radical selected from $—C(R_{11})(R_{12})—$Het, —Het, $—C(R_{11})(R_{12})—Ar$, Ar and norbornyl, $R_5$ represents a radical selected from hydrogen, hydroxyalkyl, —alk—COOalk, $—alk—CONR_7R_8$, $—alk—NR_7R_8$, alkoxy, $—CH_2Ar$, $—CH_2Het$ and alkyl, $R_6$ represents a hydroxyalkyl, —alk—COOalk, —alk—$CONR_7R_8$, $—alk—NR_7R_8$, alkoxy, $—CH_2Ar$, $—CH_2Het$ or alkyl radical, $R_7$ and $R_8$, which are identical or different, represent hydrogen or an alkyl radical or, alternatively, $R_7$ and $R_8$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_9$ and $R_{10}$, which are identical or different, represent a radical selected from hydrogen, alkyl, cycloalkyl, alkylcycloalkyl, —alk—O—alk and hydroxyalkyl or, alternatively, $R_9$ and $R_{10}$ together form with the nitrogen atom to which they are attached a 3- to 10-membered saturated or unsaturated mono- or bicyclic heterocycle, optionally containing another heteroatom chosen from oxygen, sulfur and nitrogen and being optionally substituted with one or more alkyl, —COalk, —COOalk, —CO—NHalk, oxo, hydroxyalkyl or $—CO—NH_2$ radicals, $R_{11}$ represents a radical selected from hydrogen, hydroxyalkyl, —alk—COOalk, $—alk—CONR_7R_8$, $—alk—NR_7R_8$, alkoxyalkyl, Ar, Het, $—CH_2Ar$, $—CH_2Het$ and alkyl, optionally substituted with one or more halogen atoms, $R_{12}$ represents a radical selected from hydrogen, hydroxyalkyl, —alk—COOalk, $—alk—CONR_7R_8$, $—alk—NR_7R_8$, alkoxyalkyl and alkyl, optionally substituted with one or more halogen atoms, Or, alternatively, $R_{11}$ and $R_{12}$ together form with the carbon atom to which they are attached a 3- to 10-membered saturated mono- or bicyclic ring, optionally containing another heteroatom selected from oxygen, sulfur and nitrogen and being optionally substituted with one or more alkyl radicals, Ar represents a phenyl or naphthyl radical, these different radicals being optionally substituted with one or more radicals selected from halogen, alkyl, alkoxy, —CO—alk, cyano, $—CONR_{13}R_{14}$, alkylsulfonyl, —alk—$NR_{15}R_{16}$, $—NR_{15}R_{16}$, $CF_3$, $OCF_3$, $SO_2NH_2$, hydroxyl and hydroxyalkyl, or, on 2 adjacent carbon atoms, with dioxymethylene, Het represents a heterocycle selected from benzimidazole, benzoxazole, benzothiazole, benzothiophene, thiophene, quinazoline, quinoxaline, quinoline, pyrrole, pyridine, imidazole, indole, isoquinoline, pyrimidine, thiazole, thiadiazole, furan, tetrahydrosoquinoline and tetrahydroquinoline, these heterocycles being optionally substituted with one or more substituents selected from halogen, alkyl, alkoxy, alkoxycarbonyl, oxo, hydroxyl, $OCF_3$ and $CF_3$ radicals, $R_{13}$ and $R_{14}$, which are identical or different, represent a hydrogen or alkyl radical or, alternatively, $R_{13}$ and $R_{14}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{15}$ and $R_{16}$, which are identical or different, represent a hydrogen or alkyl radical or, alternatively, $R_{15}$ and $R_{16}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, the optical isomers of these compounds and their salts with a pharmaceutically acceptable inorganic or organic acid.

4. A pharmaceutical composition according to claim 1, wherein, in the compound of formula (I), $R_1$ represents a radical $—N(R_4)—SO_2R_6$, $R_2$ represents either A) a phenyl which is unsubstituted or substituted with one or more substituents selected from halogen, alkyl, alkoxy, trifluoromethyl, trifluoromethoxy, cyano, —CONR$_7$R$_8$, hydroxyalkyl and —alk—NR$_7$R$_8$ radicals; or B) a heteroaromatic ring selected from the pyridyl,. pyrimidyl, thiazolyl and thienyl rings, it being possible for these heteroaromatic rings to be unsubstituted or substituted with a substituent selected from halogen, alkyl, alkoxy hydroxyl, trifluoromethyl, tifluoromethoxy, —CONR$_7$R$_8$ and hydroxyalkyl radicals, R$_3$ represents either A) a phenyl which is unsubstituted or substituted with one or more substituents selected from halogen, alkyl, alkoxy, trifluoromethyl, trifluoromethoxy, cyano, —CONR$_7$R$_8$, hydroxyalkyl and —alk—NR$_7$R$_8$ radicals; or B) a heteroaromatic ring selected from the pyridyl, pyrimidyl, thiazolyl and thienyl rings, it being possible for these heteroaromatic rings to be unsubstituted or substituted with a substituent selected from halogen, alkyl, alkoxy, hydroxyl, trifluoromethyl, trifluoromethoxy, —CONR$_7$R$_8$ and hydroxyalkyl, R$_4$ represents —Het or Ar, R$_6$ represents a hydroxyalkyl or alkyl radical, R$_7$ and R$_8$, which are identical or different, represent hydrogen or an alkyl radical or, alternatively, R$_7$ and R$_8$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, Ar represents a phenyl or naphthyl radical, these different radicals being optionally substituted with one or more substituents selected from halogen, alkyl, alkoxy, —CO—alk, cyano, —CONR$_{13}$R$_{14}$, —alk—NR$_{15}$R$_{16}$, —NR$_{15}$R$_{16}$, CF$_3$, OCF$_3$, SO$_2$NH$_2$, hydroxyl and hydroxyalkyl radicals, Het represents a heterocycle selected from benzimidazole, benzoxazole, benzothiazole, benzothiophene, thiophene, quinazoline, quinoxaline, quinoline, pyrrole, pyridine, imidazole, indole, isoquinoline, thiazole, thiadiazole, furan, tetrahydroisoquinoline and tetrahydroquinoline, these heterocycles being optionally substituted with one or more substituents selected from halogen, alkyl, alkoxy, alkoxycarbonyl, oxo, hydroxyl, OCF$_3$ and CF$_3$, R$_{13}$ and R$_{14}$, which are identical or different, represent hydrogen an alkyl radical or, alternatively, R$_{13}$ and R$_{14}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, R$_{15}$ and R$_{16}$, which are identical or different, represent hydrogen or an alkyl radical or, alternatively, R$_{15}$ and R$_{16}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, the optical isomers of these compounds and their salts with a pharmaceutically acceptable inorganic or organic acid.

5. A composition according to claim 1, wherein the compound of formula (I) is selected from the following compounds:

N-{1-[bis(4-chlorophenyl)methyl]azetidin-3-yl}-N-(6-chloropyrid-2-yl)methylsulfonamide, N-{1-[bis(4-chlorophenyl)methyl]azetidin-3-yl}-N-(6-ethylpyrid-2-yl)methylsulfonamide, N-{1-[bis(4-chlorophenyl)methyl]azetidin-3-yl}-N-quinol-6-ylmethylsulfonamide, N-{1-[bis(4-chlorophenyl)methyl]azetidin-3-yl}-N-quinol-5-ylmethylsulfonamide, N-{1-[bis(4-chlorophenyl)methyl]azetidin-3-yl}-N-isoquinol-5-ylmethylsulfonamide, N-{1-[bis(4-chlorophenyl)methyl]azetidin-3-yl}-N-pyrid-3-ylmethylsulfonamide, N-{1-[bis(4-chlorophenyl)methyl]azetidin-3-yl}-N-(1-oxide-pyrid-3-yl)methylsulfonamide, N-{1R,2S,4S)-bicyclo[2.2.1]hept-2-yl-N-{1-[bis(4-chlorophenyl)methyl]azetidin-3-yl}methylsulfonamide, N-{1R,2R,4S)-bicyclo[2.2.1]hept-2-yl-N-{1-[bis(4-chlorophenyl)methyl]azetidin-3-yl}methylsulfonamide, N-{1-[bis(4-chlorophenyl)methyl]azetidin-3-yl}-N-(3,5-difluorophenyl)methylsulfonamide, N-{1-[bis(4-chlorophenyl)methyl]azetidin-3-yl}-N-(thiazol-2-yl)methylsulfonamide, N-{1-[bis(4-chlorophenyl)methyl]azetidin-3-yl}-N-(3-methoxyphenyl)methylsulfonamide, N-{1-[bis(4-chlorophenyl)methyl]azetidin-3-yl}-N-(3-hydroxyphenyl)methylsulfonamide, N-{1-[bis(4-chlorophenyl)methyl]azetidin-3-yl}-N-(3-hydroxymethylphenyl)methylsulfonamide, Ethyl N-{1-[bis(4-chlorophenyl)methyl]azetidin-3-yl}-N-(methylsulfonyl)-3-aminobenzoate, N-{1-[bis(4-chlorophenyl)methyl]azetidin-3-yl}-N-(1-isobutylpiperid-4-yl)methylsulfonamide, N-benzyl-N-{1-[bis(4-chlorophenyl)methyl]azetidin-3-yl}amine, N-{1-[bis(4-chlorophenyl)methyl]azetidin-3-yl}-N-(3,5-difluorobenzyl)amine, N-{1-[bis(4-chlorophenyl)methyl]azetidin-3-yl}-N-(3,5-difluorobenzyl)methylsulfonamide, N-{1-[bis(4-chlorophenyl)methyl]azetidin-3-yl}-N-(pyrid-3-ylmethyl)methylsulfonamide, N-{1-[bis(4-fluorophenyl)methyl]azetidin-3-yl}-N-(3,5-difluorophenyl)methylsulfonamide, (RS)-N-{1-[(4-chlorophenyl)pyrid-3-ylmethyl]azetidin-3-yl}-N-(3,5-difluorophenyl)methylsulfonamide, (R)-N-{1-[(4-chlorophenyl)pyrid-3-ylmethyl]azetidin-3-yl}-N-(3,5-difluorophenyl)methylsulfonamide, (S)-N-{1-[(4-chlorophenyl)pyrid-3-ylmethyl]azetidin-3-yl}-N-(3,5-difluorophenyl)methylsulfonamide, (RS)-N-{1-[(4-chlorophenyl)pyrid-4-ylmethyl]azetidin-3-yl}-N-(3,5-difluorophenyl)methylsulfonamide, (R)-N-{1-[(4-chlorophenyl)pyrid-4-ylmethyl]azetidin-3-yl}-N-(3,5-difluorophenyl)methylsulfonamide, (S)-N-{1-[(4-chlorophenyl)pyrid-4-ylmethyl]azetidin-3-yl}-N-(3,5-difluorophenyl)methylsulfonamide, (RS)-N-{1-[(4-chlorophenyl)pyrimidin-5-ylmethyl]-azetidin-3-yl}-N-(3,5-difluorophenyl)methylsulfonamide, (R)-N-{1-[(4-chlorophenyl)pyrimidin-5-ylmethyl]-azetidin-3-yl}-N-(3,5-difluorophenyl)methylsulfonamide, (S)-N-{1-[(4-chlorophenyl)pyrimidin-5-ylmethyl]-azetidin-3-yl}-N-(3,5-difluorophenyl) methylsulfonamide,
N-{1-[bis(4-chlorophenyl)methyl]azetidin-3-yl}-N-(3,5-difluorophenyl)benzylsulfonamide, their optical isomers and their pharmaceutically acceptable salts.

6. A compound of formula:

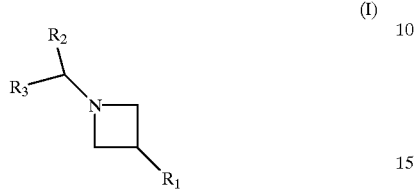

(I)

in which
R$_1$ represents a radical —N(R$_4$)R$_5$, —N(R$_4$)—CO—R$_5$, or —N(R$_4$)—SO$_2$R$_6$, R$_2$ and R$_3$, which are identical or different, represent either A) an aromatic group selected from phenyl, naphthyl and indenyl, these aromatic groups being unsubstituted or substituted with one or more substituents selected from halogen, alkyl, alkoxy, formyl, hydroxyl, trifluoromethyl, trifluoromethoxy, —CO—alk, cyano, —COOH, COOalk, —CONR$_7$R$_8$, —CO—NH—NR$_9$R$_{10}$, alkylsulfanyl, alkylsulfinyl, alkylsulfonyl, alkylsulfanylalkyl, alkylsulfinylalkyl, alkylsulfonylalkyl, hydroxyalkyl and —alk—NR$_7$R$_8$ radicals; or B) a heteroaromatic ring selected from benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidyl, quinolyl, 1,2,3,4-tetrahydroisoquinolyl, thiazolyl and thienyl rings, it being possible for these heteroaromatic rings to be unsubstituted or substituted with a substituent selected from halogen, alkyl, alkoxy, hydroxyl, trifluoromethyl, trifluoromethoxy, cyano, —COOH, COOalk, —CO—NH—NR$_9$R$_{10}$, —CONR$_7$R$_8$, —alk—NR$_9$R$_{10}$, alkylsulfanyl, alkylsulfinyl, alkylsulfonyl, alkylsulfanylalkyl, alkylsulfinylalkyl, alkylsulfonylalkyl and hydroxyalkyl, R$_4$ represents a radical selected from—C(R$_{11}$)(R$_{12}$)—Het, —Het, —(CR$_{11}$)(R$_{12}$)—Ar, Ar, cycloalkyl and norbornyl, R$_5$ represents a radical selected from hydrogen, hydroxyalkyl, —alk—COOalk, —alk—CONR$_7$R$_8$, —alk—NR$_7$R$_8$, alkoxy, Ar, Het, —CH$_2$Ar, —CH$_2$Het and alkyl, optionally substituted with one or more halogens, R$_6$ represents a hydroxyalkyl, —alk—COOalk, —alk—CONR$_7$R$_8$, —alk—NR$_7$R$_8$, alkoxy, Ar, Het, —CH$_2$Ar, —CH$_2$Het or alkyl radical optionally substituted with 1 or more halogens, R$_7$ and R$_8$, which are identical or different, represent hydrogenor alkyl radical or, alternatively, R$_7$ and R$_8$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, R$_9$ and R$_{10}$, which are identical or different, represent a radical selected from hydrogen, alkyl, —COOalk, cycloalkyl, alkylcycloalkyl, —alk—O—alk and hydroxyalkyl or, alternatively, R$_9$ and R$_{10}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, —COalk, —COOalk, —CO—NHalk, —CS—NHalk, oxo, hydroxyalkyl, —alk—O—alk or —CO—NH$_2$ radicals R$_{11}$ represents a radical selected from hydrogen, hydroxyalkyl, —alk—COOalk, —alk—CONR$_7$R$_8$, —alk—NR$_7$R$_8$, alkoxyalkyl, Ar, Het, —CH$_2$Ar, —CH$_2$Het and alkyl optionally substituted with one or more halogens, R$_{12}$ represents a radical selected from hydrogen, hydroxyalkyl, —alk—COOalk, —alk—CONR$_7$R$_8$, —alk—NR$_7$R$_8$, alkoxyalkyl or alkyl optionally substituted with one or more halogens, or alternatively R$_{11}$ and R$_{12}$ together form with the carbon atom to which they are attached a 3- to 10-membered saturated mono- or bicyclic ring, optionally containing a heteroatom selected from oxygen, sulfur and nitrogen and being optionally substituted with one or more alkyl radicals, Ar represents a phenyl, naphthyl or indenyl radical, these different radicals being optionally substituted with one or more radicals selected from halogen, alkyl, alkoxy, —COalk, cyano, —COOH, —COOalk, —CONR$_{13}$R$_{14}$, —CO—NH—NR$_{15}$R$_{16}$, alkylsulfanyl, alkylsulfinyl, alkylsulfonyl, —alk—NR$_{15}$R$_{16}$, —NR$_{15}$R$_{16}$, alkylthioalkyl, formyl, CF$_3$, OCF$_3$, Het, —O—alk—NH—cycloalkyl, SO$_2$NH$_2$, hydroxyl, hydroxyalkyl, —NHCOalk, and NHCOOalk or, on 2 adjacent carbon atoms, with dioxymethylene, Het represents a 3- or 10-membered unsaturated or saturated mono- or bicyclic heterocycle containing one ore more heteroatoms selected from oxygen, sulfur and nitrogen optionally substituted with one or more substituents selected from halogen, alkyl, alkoxy, alkoxycarbonyl, oxo and hydroxyl, the nitrogen-containing heterocycles being optionally in their N-oxidized form, R$_{13}$ and R$_{14}$, which are identical or different, represent hydrogen or an alkyl radical or, alternatively, R$_{13}$ and R$_{14}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, R$_{15}$ and R$_{16}$, which are identical or different, represent hydrogen or an alkyl radical or, alternatively, R$_{15}$ and R$_{16}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, alk represents an alkyl or alkylene radical, the alkyl and alkylene radicals and portions and the alkoxy radicals and portions are in the form of a straight or branched chain containing 1 to 6 carbon atoms and the cycloalkyl radicals contain 3 to 10 carbon atoms, the optical isomers of these compounds and their salts with a pharmaceutically acceptable inorganic or organic acid, with the exception of benzhydryl-1-cyclopropylamino-3-azetidine dichlorohydrate; 2-[2-((1-(benzhydryl)-azetidine-3-yl)-2-amino)-phenyl]-ethanol; and 1-diphenylmethyl-3-((2-hydroxymethyl)phenylamino)azetidine, as well as any compound in which $R_2$ and $R_3$ represent phenyl radicals, $R_1$ represents a radical —N($R_4$)$SO_2R_6$ in which $R_4$ represents a phenyl radical and $R_6$ represents a methyl radical.

7. A compound of formula (I) according to claim 6, wherein Het is a heterocycle selected from benzimidazole, benzoxazole, benzothiazole, benzothiophene, cinnoline, thiophene, quinazoline, quinoxaline, quinoline, pyrazole, pyrrole, pyridine, imidazole, indole, isoquinoline, pyrimidine, thiazole, thiadiazole, piperidine, piperazine, triazole, furan, tetrahydroisoquinoline, and tetrahydroquinoline, these heterocycles being optionally substituted with one or more substituents selected from halogen, alkyl, alkoxy, alkoxycarbonyl, oxo, hydroxyl, $OCF_3$ and $CF_3$.

8. A compound of formula:

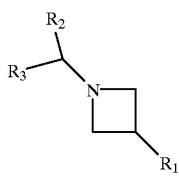

(I)

wherein $R_1$ represents a radical —N($R_4$)$R_5$ or —N($R_4$)—$SO_2R_6$, $R_2$ represents either A) a phenyl which is unsubstituted or substituted with one or more substituents selected from halogen, alkyl, alkoxy, trifluoromethyl, trifluoromethoxy, —CO—alk, cyano, —CONR$_7$R$_8$, hydroxyalkyl and —alk—NR$_7$R$_8$ radicals; or B) a heteroaromatic ring selected from the pyridyl, pyrimidyl, thiazolyl and thienyl rings, it being possible for these heteroaromatic rings to be unsubstituted or substituted with a substituent selected from halogen, alkyl, alkoxy, hydroxyl, trifluoromethyl, trifluoromethoxy, —CONR$_7$R$_8$, —alk—NR$_9$R$_{10}$, alkylsulfanyl, alkylsulfinyl, alkylsulfonyl and hydroxyalkyl, $R_3$ represents either A) a phenyl which is unsubstituted or substituted with one or more substituents selected from halogen, alkyl, alkoxy, trifluoromethyl, trifluoromethoxy, —CO—alk, cyano, —CONR$_7$R$_8$, hydroxyalkyl and —alk—NR$_7$R$_8$ radicals; or B) a heteroaromatic ring selected from the pyridyl, pyrimidyl, thiazolyl and thienyl rings, it being possible for these heteroaromatic rings to be unsubstituted or substituted with a radical selected from halogen, alkyl, alkoxy, hydroxyl, trifluoromethyl, trifluoromethoxy, —CONR$_7$R$_8$, —alk—NR$_9$R$_{10}$, alkylsulfanyl, alkylsulfinyl, alkylsulfonyl and hydroxyalkyl,$R_4$ represents a radical selected from —C($R_{11}$)($R_{12}$)—Het, —Het, —C($R_{11}$)($R_{12}$)—Ar, Ar and norbornyl, $R_5$ represents a radical selected from hydrogen, hydroxyalkyl, —alk—COOalk, —alk—CONR$_7$R$_8$, —alk—NR$_7$R$_8$, alkoxy, —CH$_2$Ar, —CH$_2$Het and alkyl, $R_6$ represents a hydroxyalkyl, —alk—COOalk, —alk—CONR$_7$R$_8$, —alk—NR$_7$R$_8$, alkoxy, —CH$_2$Ar, —CH$_2$Het or alkyl radical, $R_7$ and $R_8$, which are identical or different, represent hydrogen or an alkyl radical or, alternatively, $R_7$ and $R_8$ together form with the nitrogen atom to which they are attached a 3- or 10-membered saturated mono- or bicyclic heterocycle, optionally containing another heteroatom selected from oxygen, sulfur and nitrogen and being optionally substituted with one or more alkyl radicals, $R_9$ and $R_{10}$, which are identical or different, represent a radical selected from hydrogen, alkyl, cycloalkyl, alkylcycloalkyl, —alk—O—alk and hydroxyalkyl or, alternatively, $R_9$ and $R_{10}$ together form with the nitrogen atom to which they are attached a 3- to 10-membered saturated or unsaturated mono- or bicyclic heterocycle, optionally containing another heteroatom selected from oxygen, sulfur and nitrogen and being optionally substituted with one or more alkyl, —COalk, —COOalk, —CO—NHalk, oxo, hydroxyalkyl or —CO—NH$_2$ radicals, $R_{11}$ represents a radical selected from hydrogen, hydroxyalkyl, —alk—COOalk, —alk—CONR$_7$R$_8$, —alk—NR$_7$R$_8$, alkoxyalkyl, Ar, Het, —CH$_2$Ar, —CH$_2$Het and alkyl optionally substituted with one or more halogen atoms, $R_{12}$ represents a radical selected from hydrogen, hydroxyalkyl, —alk—COOalk, —alk—CONR$_7$R$_8$, —alk—NR$_7$R$_8$, alkoxyalkyl and alkyl optionally substituted with one or more halogen atoms, or, alternatively, $R_{11}$ and $R_{12}$ together form with the carbon atom to which they are attached a 3- to 10-membered saturated mono- or bicyclic ring, optionally containing another heteroatom selected from oxygen, sulfur and nitrogen and being optionally substituted with one or more alkyl radicals, Ar represents a phenyl or naphthyl radical, these different radicals being optionally substituted with one or more substituents selected from halogen, alkyl, alkoxy, —CO—alk, cyano, —CONR$_{13}$R$_{14}$, alkylsulfonyl, —alk—NR$_{15}$R$_{16}$, —NR$_{15}$R$_{16}$, CF$_3$, OCF$_3$, SO$_2$NH$_2$, hydroxyl and hydroxyalkyl radicals or, on 2 adjacent carbon atoms, with dioxymethylene, Het represents a heterocycle selected from benzimidazole, benzoxazole, benzothiazole, benzothiophene, thiophene, quinazoline, quinoxaline, quinoline, pyrrole, pyridine, imidazole, indole, isoquinoline, pyrimidine, thiazole, thiadiazole, furan, tetrahydroisoquinoline and tetrahydroquinoline, these heterocycles being optionally substituted with one or more substituents selected from halogen, alkyl, alkoxy, alkoxycarbonyl, oxo, hydroxyl, OCF$_3$ and CF$_3$ radicals, $R_{13}$ and $R_{14}$, which are identical or different, represent hydrogen or an alkyl radical or, alternatively, $R_{13}$ and $R_{14}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{15}$ and $R_{16}$, which are identical or different, represent hydrogen or an alkyl radical or, alternatively, $R_{15}$ and $R_{16}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, the optical isomers of these compounds and their salts with a pharmaceutically acceptable inorganic or organic acid, with the exception of any compound in which $R_2$ and $R_3$ represent phenyl radicals, $R_1$ represents a radical —N($R_4$)SO$_2R_6$ in which $R_4$ represents a phenyl radical and $R_6$ represents a methyl radical.

9. A compound of formula (I) according to claim 8, wherein $R_1$ represents a radical —N($R_4$)—SO$_2R_6$, $R_2$ represents either A) a phenyl which is unsubstituted or substituted with one or more substituents selected from halogen, alkyl, alkoxy, trifluoromethyl, trifluoromethoxy, cyano, —CONR$_7$R$_8$, hydroxyalkyl and —alk—NR$_7$R$_8$ radicals; or B) a heteroaromatic chosen from the pyridyl, pyrimidyl, thiazolyl and thienyl rings, it being possible for these heteroaromatics to be unsubstituted or substituted with a halogen atom or an alkyl, alkoxy, hydroxyl, trifluoromethyl, trifluoromethoxy, —CONR$_7$R$_8$ or hydroxyalkyl radical, $R_3$ represents either (1) a phenyl which is unsubstituted or substituted with one or more substituents selected from halogen, alkyl, alkoxy, trifluoromethyl, trifluoromethoxy, cyano, —CONR$_7$R$_8$, hydroxyalkyl and —alk—NR$_7$R$_8$ radicals; or a heteroaromatic ring selected from the pyridyl, pyrimidyl, thiazolyl and thienyl rings, it being possible for these heteroaromatic rings to be unsubstituted or substituted with a substituent selected from halogen, alkyl, alkoxy, hydroxyl, trifluoromethyl, trifluoromethoxy, —CONR$_7$R$_8$ and hydroxyalkyl, $R_4$ represents —Het or Ar, $R_6$ represents a hydroxyalkyl or alkyl radical, $R_7$ and $R_8$, which are identical or different, represent hydrogen or an alkyl radical or, alternatively, $R_7$ and $R_8$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, Ar represents a phenyl or naphthyl radical, these different radicals being optionally substituted with one or more substituents selected from halogen, alkyl, alkoxy, —CO—alk, cyano, —CONR$_{13}$R$_{14}$, —alk—NR$_{15}$R$_{16}$, —NR$_{15}$R$_{16}$, CF$_3$, OCF$_3$, SO$_2$NH$_2$, hydroxyl and hydroxyalkyl radicals, Het represents a heterocycle selected from benzimidazole, benzoxazole, benzothiazole, benzothiophene, thiophene, quinazoline, quinoxaline, quinoline, pyrrole, pyridine, imidazole, indole, isoquinoline, thiazole, thiadiazole, furan, tetrahydroisoquinoline and tetrahydroquinoline, these heterocycles being optionally substituted, with one or more substituents selected from halogen, alkyl, alkoxy, alkoxycarbonyl, oxo, hydroxyl, OCF$_3$ and CF$_3$ radicals, $R_{13}$ and $R_{14}$, which are identical or different, represent hydrogen, or an alkyl radical or, alternatively, $R_{13}$ and $r_{14}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, $R_{15}$ and $R_{16}$, which are identical or different, represent hydrogen, or an alkyl radical or, alternatively, $R_{15}$ and $R_{16}$ together form with the nitrogen atom to which they are attached a 3- to 10-membered saturated mono- or bicyclic heterocycle, optionally containing another heteroatom selected from oxygen, sulfur and nitrogen and being optionally substituted with one or more alkyl radicals, the optical isomers of these compounds and their salts with a pharmaceutically acceptable inorganic or organic acid, with the exception of any compound in which $R_2$ and $R_3$ represent phenyl radicals, $R_1$ represents a radical —N($R_4$)SO$_2R_6$ in which $R_4$ represents a phenyl radical and $R_6$ represents a methyl radical.

10. A compound of formula (I) according to claim 8, selected from the following compounds:

N-{1-[bis(4-chlorophenyl)methyl]azetidin-3-yl}-N-(6-chloropyrid-2-yl)methylsulfonamide, N-{1-[bis(4-chlorophenyl)methyl]azetidin-3-yl}-N-(6-ethylpyrid-2-yl)methylsulfonamide, N-{1-[bis(4-chlorophenyl)methyl]azetidin-3-yl}-N-quinol-6-ylmethylsulfonamide, N-{1-[bis(4-chlorophenyl)methyl]azetidin-3-yl}-N-quinol-5-ylmethylsulfonamide, N-{1-[bis(4-chlorophenyl)methyl]azetidin-3-yl}-N-isoquinol-5-ylmethylsulfonamide, N-{1-[bis(4-chlorophenyl)methyl]azetidin-3-yl}-N-pyrid-3-ylmethylsulfonamide, N-{1-[bis(4-chlorophenyl)methyl]azetidin-3-yl}-N-(1-oxide-pyrid-3-yl)methylsulfonamide, N-{1R,2S,4S)-bicyclo[2.2.1]hept-2-yl-N-{1-[bis(4-chlorophenyl)methyl]azetidin-3-yl}methylsulfonamide, N-{1R,2R,4S)-bicyclo[2.2.1]hept-2-yl-N-{1-[bis(4-chlorophenyl)methyl]azetidin-3-yl}methylsulfonamide, N-{1-[bis(4-chlorophenyl)methyl]azetidin-3-yl}-N-(3,5-difluorophenyl)methylsulfonamide, N-{1-[bis(4-chlorophenyl)methyl]azetidin-3-yl}-N-(thiazol-2-yl)methylsulfonamide, N-{1-[bis(4-chlorophenyl)methyl]azetidin-3-yl}-N-(3-methoxyphenyl)methylsulfonamide, N-{1-[bis(4-chlorophenyl)methyl]azetidin-3-yl}-N-(3-hydroxyphenyl)methylsulfonamide, N-{1-[bis(4-chlorophenyl)methyl]azetidin-3-yl}-N-(3-hydroxymethylphenyl)methylsulfonamide, Ethyl N-{1-[bis(4-chlorophenyl)methyl]azetidin-3-yl}-N-(methylsulfonyl)-3-aminobenzoate, N-{1-[bis(4-chlorophenyl)methyl]azetidin-3-yl}-N-(1-isobutylpiperid-4-yl)methylsulfonamide, N-benzyl-N-{1-[bis(4-chlorophenyl)methyl]azetidin-3-yl}amine, N-{1-[bis(4-chlorophenyl)methyl]azetidin-3-yl}-N-(3,5-difluorobenzyl)amine, N-{1-[bis(4-chlorophenyl)methyl]azetidin-3-yl}-N-(3,5-difluorobenzyl)methylsulfonamide, N-{1-[bis(4-chlorophenyl)methyl]azetidin-3-yl}-N-(pyrid-3-ylmethyl)methylsulfonamide, N-{1-[bis(4-fluorophenyl)methyl]azetidin-3-yl}-N-(3,5-difluorophenyl)methylsulfonamide, (RS)-N-{1-[(4-chlorophenyl)pyrid-3-ylmethyl]azetidin-3-yl}-N-(3,5-difluorophenyl)methylsulfonamide, (R)-N-{1-[(4-chlorophenyl)pyrid-3-ylmethyl]azetidin-3-yl}-N-(3,5-difluorophenyl)methylsulfonamide, (S)-N-{1-[(4-chlorophenyl)pyrid-3-ylmethyl]azetidin-3-yl}-N-(3,5-difluorophenyl)methylsulfonamide,
(RS)-N-{1-[(4-chlorophenyl)pyrid-4-ylmethyl]azetidin-3-yl}-N-(3,5-difluorophenyl)methylsulfonamide,
(R)-N-{1-[(4-chlorophenyl)pyrid-4-ylmethyl]azetidin-3-yl}-N-(3,5-difluorophenyl)methylsulfonamide,
(S)-N-{1-[(4-chlorophenyl)pyrid-4-ylmethyl]azetidin-3-yl}-N-(3,5-difluorophenyl)methylsulfonamide,
(RS)-N-{1-[(4-chlorophenyl)pyrimidin-5-ylmethyl]-azetidin-3-yl}-N-(3,5-difluorophenyl)methylsulfonamide,
(R)-N-{1-[(4-chlorophenyl)pyrimidin-5-ylmethyl]-azetidin-3-yl}-N-(3,5-difluorophenyl)methylsulfonamide,
(S)-N-{1-[(4-chlorophenyl)pyrimidin-5-ylmethyl]-azetidin-3-yl}-N-(3,5-difluorophenyl)methylsulfonamide,
N-{1-[bis(4-chlorophenyl)methyl]azetidin-3-yl}-N-(3,5-difluorophenyl)benzylsulfonamide, their optical isomers and their salts with a pharmaceutically acceptable inorganic or organic acid.

11. N-{1-[bis-(4-chlorophenyl)methyl]-azetidin-3-yl}-N-(3,5-difluorophenyl)methylsulfonamide, its optical isomers and its salts with a pharmaceutically acceptable inorganic or organic acid.

12. A process for preparing a compound of formula (I) according to claim 6, for which $R_1$ represents a radical $—N(R_4)R_5$ in which $R_5$ is a hydrogen atom, $R_4$ is a radical $—CR_{11}R_{12}—Ar$ or $—CR_{11}R_{12}—Het$ and $R_{12}$ is a hydrogen atom, the process comprising reacting a derivative $Rb—COR_{11}$ for which $R_{11}$ has the same meanings as in claim 6 with a derivative of formula:

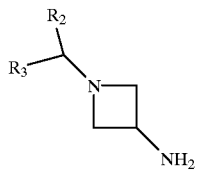

wherein Rb represents a radical Ar or Het, and $R_2$, $R_3$, $R_{11}$ Ar and Het have the same meanings as in claim 6, isolating the product and optionally converting the product to a pharmaceutically acceptable salt.

13. A process for preparing a compound of formula (I) according to claim 6, for which $R_1$ represents a radical $—N(R_4)—CO—R_5$ in which $R_4$ is a radical $—C(R_{11})(R_{12})—Het$ or $—C(R_{11})(R_{12})—Ar$ and $R_{12}$ is a hydrogen atom, the process comprising reacting a derivative Hal—$COR_5$ with a derivative of formula:

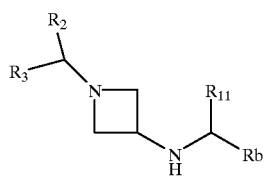

wherein Hal represents a halogen atom Rb represents a radical Ar or Het, and $R_2$, $R_3$, $R_5$, $R_{11}$, Ar and Het have the same meanings as in claim 6, isolating the product and optionally converting the product to a pharmaceutically acceptable salt.

14. A process for preparing a compound of formula (I) according to claim 6, for which $R_1$ represents a radical $—N(R_4)—SO_2R_6$ in which $R_4$ is a radical $—C(R_{11})(R_{12})—Ar$ or $—C(R_{11})(R_{12})—Het$ and $R_{12}$ is a hydrogen atom, the process comprising reacting a derivative Hal-$SO_2R_6$ with a derivative of formula:

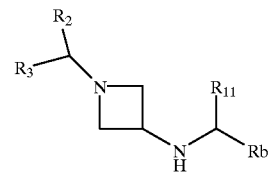

wherein $R_2$, $R_3$, $R_{11}$ and $R_5$ have the same meanings as in claim 6, Hal represents a halogen atom and Rb represents a radical Ar or Het, isolating the product and optionally converting the product to a pharmaceutically acceptable salt.

15. A process for preparing a compound of formula (I) according to claim 6 for which $R_1$ represents a radical $—N(R_4)R_5$, the process comprising reacting a derivative $R_5(R_4)NH$ with a derivative of formula:

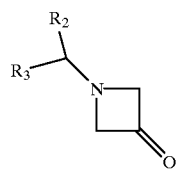

wherein, $R_2$, $R_3$, $R_4$ and $R_5$ have the same meanings as in claim 6, isolating the product and optionally converting the product to a pharmaceutically acceptable salt.

16. A process for preparing a compound of formula (I) according to claim 6 for which $R_1$ represents a radical $—N(R_4)SO_2R_6$, the process comprising reacting a derivative Hal—$SO_2R_6$ with a derivative of formula:

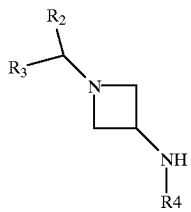

wherein $R_2$, $R_3$, $R_4$ and $R_6$ have the same meanings as in claim 6 and Hal represents a halogen atom, isolating the product and optionally converting the product to a pharmaceutically acceptable salt.

17. A process for preparing a compound of formula (I) according to claim 6 for which $R_1$ represents a radical $—N(R_4)COR_5$, the process comprising reacting a derivative Hal—$COR_6$ with a derivative of formula:

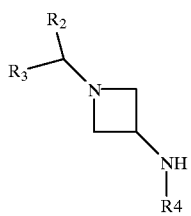

wherein $R_2$, $R_3$, $R_4$ and $R_5$ have the same meanings as in claim 6 and Hal represents a halogen atom, isolating the product and optionally converting the product to a pharmaceutically acceptable salt.

18. A process for preparing a compound of formula (I) according to claim 6 for which $R_1$ represents a radical —N($R_4$)—SO$_2$—$R_6$ in which $R_4$ is a radical Het or Ar, the process comprising reacting a derivative Rd—NH—SO$_2$—$R_6$ with a derivative of formula:

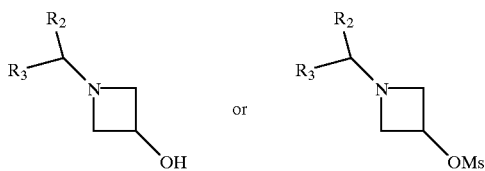

wherein Rd represents a radical Ar or Het; $R_2$, $R_3$ and $R_6$ have the same meanings as in claim 6; and Ms represents a methylsulfonyloxy radical, isolating the product and optionally converting the product to a pharmaceutically acceptable salt.

19. A process for preparing a compound of formula (I) according to claim 6, the process comprising reacting a derivative $R_2$—CHBr—$R_3$ with a derivative of formula:

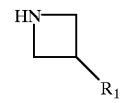

wherein $R_1$, $R_2$ and $R_3$ have the same meanings as in claim 6, isolating the product and optionally converting the product to a pharmaceutically acceptable salt.

20. A process for preparing a compound of formula (I) according to claim 6 for which $R_1$ represents a radical —N($R_4$)—SO$_2$—$R_6$ in which $R_4$ is a piperid-4-yl radical substituted on the nitrogen with an alkyl radical, the process comprising alkylating a corresponding compound of formula (I) for which $R_1$ represents a radical —N($R_4$)—SO$_2$—$R_6$ in which $R_4$ is a piperid-4-yl radical, isolating the product and optionally converting the product to a pharmaceutically acceptable salt.

21. A process for preparing a compound of formula (I) according to claim 6, for which $R_1$ represents a radical —N($R_4$)—SO$_2$—$R_6$ in which $R_4$ is a phenyl radical substituted with a pyrrolid-1-yl radical, the process comprising reacting pyrrolidine with a corresponding compound of formula (I) in which $R_1$ represents a radical —N($R_4$)SO$_2$$R_6$ for which $R_4$ is a phenyl radical substituted with a halogen atom, isolating the product and optionally converting the product to a pharmaceutically acceptable salt.

* * * * *